United States Patent
Jorand-Lebrun et al.

(10) Patent No.: US 7,115,754 B2
(45) Date of Patent: Oct. 3, 2006

(54) PYRROLIDINE DERIVATIVES AS OXYTOCIN ANTAGONISTS

(75) Inventors: Catherine Jorand-Lebrun, Contamine-Sarzin (FR); Jerome Dorbais, Annecy (FR); Anna Quattropani, Geneva (CH); Matthias Schwarz, Geneva (CH); Delphine Valognes, Asson (FR)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 10/518,543

(22) PCT Filed: Jul. 4, 2003

(86) PCT No.: PCT/EP03/50286

§ 371 (c)(1),
(2), (4) Date: Jul. 11, 2005

(87) PCT Pub. No.: WO2004/005249

PCT Pub. Date: Jan. 15, 2004

(65) Prior Publication Data

US 2006/0004020 A1    Jan. 5, 2006

(30) Foreign Application Priority Data

Jul. 5, 2002    (EP) ................... 02100784

(51) Int. Cl.
*C07D 207/09*    (2006.01)
*C07D 207/18*    (2006.01)
*A01N 43/36*    (2006.01)

(52) U.S. Cl. .................. 548/539; 514/326; 514/333; 514/426; 514/424; 548/406; 548/557; 548/566; 548/571; 548/544; 546/208

(58) Field of Classification Search ................ 514/326, 514/333; 548/539, 406, 557, 566, 571; 546/208
See application file for complete search history.

(56) References Cited

FOREIGN PATENT DOCUMENTS

WO    99 52868    10/1999
WO    01 72705    10/2001

OTHER PUBLICATIONS

Maggi, Marlo et al. "Human Myometrium during Pregnancy Contains and Responds to V1 Vasopressin Receptors as well as Oxytocin Receptors", Journal of Clinical Endocrinology and Metabolism, vol. 70, No. 4, pp. 1142-1154 1990.

Mitchell, B. F. et al. "Oxytocin and its Receptor in the Process of Parturition", J. Soc. Gynecol. Investig. vol. 8, No. 3, pp. 122-133 2001.

Thornton, Steven et al. "Oxytocin antagonists: clinical and scientific considerations", Experimental Physiology, vol. 86, No. 2, pp. 297-302 2001.

Evans, Ben E. et al. "Orally Active, Nonpeptide Oxytocin Antagonists", J. Med. Chem. vol. 35, pp. 3919-3927 1992.

Cook, Neil et al. "SPA: a revolutionary new technique for drug screening", Pharmaceutical Manufacturing International, pp. 49-53 1992.

Gimpl, Gerald et al. The Oxytocin Receptor System: Structure, Function, and Regulation, vol. 81, No. 2, pp. 629-683 2001.

*Primary Examiner*—Joseph K. McKane
*Assistant Examiner*—Yong Chu
(74) *Attorney, Agent, or Firm*—Oblon, Spivak, McClelland, Maier & Neustadt, P.C.

(57) ABSTRACT

The present invention relates to novel pyrrolidine derivative of formula (I), its geometrical isomers, its optically active forms as enantiomers, diastereomers, mixtures of these and its racemate forms, as well as salts thereof, wherein $R^1$ is selected from the group comprising or consisting of H and $C_1$–$C_6$-alkyl, for the prevention and/or treatment of preterm labor, premature birth or dysmenorrhea

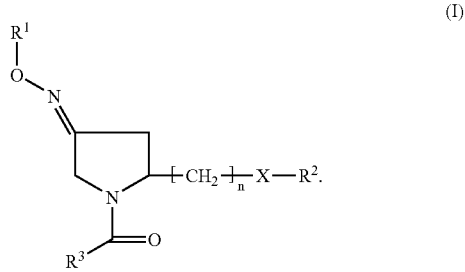

11 Claims, No Drawings

PYRROLIDINE DERIVATIVES AS OXYTOCIN ANTAGONISTS

CROSS REFERENCES TO RELATED APPLICATIONS

This application is a national stage application of International Patent Application No. PCT/EP03/50286, filed on Jul. 4, 2003, and claims priority to European Patent Application No. 02100784.4, filed on Jun. 5, 2002, both of which are incorporated herein by reference in their entireties.

FIELD OF THE INVENTION

The present invention is directed to novel pyrrolidine derivatives, in particular for use as medicaments, as well as pharmaceutical formulations containing such pyrrolidine derivatives. Said pyrrolidine derivatives are useful in the treatment and/or prevention of preterm labor, premature birth, dysmenorrhea. Preferably, the pyrrolidine derivatives display a modulatory, notably an antagonist activity of the oxytocin receptor. More preferably, said compounds are useful in the treatment and/or prevention of disease states mediated by oxytocin, including preterm labor, premature birth and dysmenorrhea.

BACKGROUND OF THE INVENTION

Oxytocin (OT) is a cyclic nona-peptide whose actions are mediated by activation of specific G protein-coupled receptors currently classified into OT receptors (OT-R) (1).

Oxytocin (OT) causes the contraction of the uterus of mammals during labor. The corresponding oxytocin receptor belongs to the family of G-protein-coupled receptors and is similar to $V_1$ and $V_2$ vasopressin receptors. OT receptors increase dramatically during the course of pregnancy. The concentration of OT receptors has been shown to correlate with spontaneous uterine activity (2–3). OT-induced contractions of the uterus during labor result in the dilatation of the cervix and eventually in the movement of the foetus through the vaginal canal. In some cases, these contractions occur before the foetus is fully viable, resulting in premature labor. Premature labor and premature birth are undesired as they are major causes of perinatal morbidity. Hence, the management of preterm labor represents a significant problem in the field of obstetrics.

In recent years, strong evidence has accumulated indicating that the hormone oxytocin plays a major role in initiating labor in mammals, in particular in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterus could be blocked. An oxytocin modulator, e.g. blocker or antagonist would likely be efficacious for treating preterm labor.

A further condition related to oxytocin is dysmenorrhea, which is characterised by pain or discomfort associated with menses. The pain is believed to result from uterine contractions and ischemia, probably mediated by the effect of prostaglandins produced in the secretory endometrium. By blocking both the indirect and direct effects of oxytocin on the uterus, an oxytocin antagonist would be a likely candidate for treating dysmenorrhea.

Some agents counteracting the action of oxytocin are currently used in clinical studies (4). Such tocolytic agents (i.e. uterine-relaxing agents) include beta-2-adrenergic agonists, magnesium sulfate and ethanol. The leading beta-2-adrenergic agonist is Ritodrine, which causes a number of cardiovascular and metabolic side effects, including tachycardia, increased renin secretion, hyperglycemia and reactive hypoglycemia in the infant. Further beta-2-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmiss-ion, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

Atosiban, a peptide OT antagonist, suffers the problem of most peptides: low oral bioavailability resulting from intestinal degradation. Such compounds must be administered parenterally.

The development of non-peptide ligands for peptide hormone receptors is expected to overcome this problem. Small molecule selective oxytocin antagonists have been reported by Merck. In addition to cyclic hexapeptides, Merck suggested indanylpiperidines and tolylpiperazines as orally deliverable OT antagonists (5). In WO 96/22775 and U.S. Pat. No. 5,756,497, Merck reported benzoxazinylpiperidines or benzoxazinones as OT receptor antagonists.

Specific sulfonamides have been reported to antagonize ocytocin at the ocytocin receptor. Elf Sanofi's EP-A-0469984 and EP-A-0526348 report N-sulfonyl indolines acting as antagonists of the vasopressin and the oxytocin receptors.

American Cyanamid's U.S. Pat. No. 5,889,001 claims pyrazole benzodiazepine derivatives as vasopressin and oxytocin antagonists.

Recent pyrrolidine derivatives, such as pyrrolidine amides and pyrrolidines substituted with fused heteroaryl were developed as oxytocin receptor antagonists (WO 01/72705).

SUMMARY OF THE INVENTION

In a first aspect, the invention provides novel pyrrolidine derivatives of formula I:

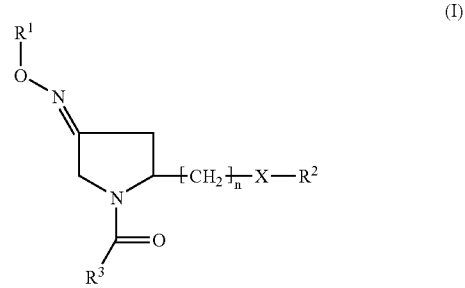

(I)

$R^1$ in formula (I) is selected from the group consisting of H and substituted or unsubstituted $C_1$–$C_6$-alkyl. Preferably $R^1$ is H or methyl.

$R^2$ in formula (I) is selected from the group consisting of hydrogen, substituted or unsubstituted $C_1$–$C_6$-alkyl, substituted or unsubstituted $C_1$–$C_6$-alkyl aryl, substituted or unsubstituted heteroaryl, substituted or unsubstituted $C_1$–$C_6$-alkyl heteroaryl, substituted or unsubstituted $C_2$–$C_6$-alkenyl, substituted or unsubstituted $C_2$–$C_6$-alkenyl aryl, substituted or unsubstituted $C_2$–$C_6$-alkenyl heteroaryl, substituted or unsubstituted $C_2$–$C_6$-alkynyl, substituted or unsubstituted $C_2$–$C_6$-alkynyl aryl, substituted or unsubstituted $C_2$–$C_6$-alkynyl heteroaryl, substituted or unsubstituted $C_3$–$C_8$-cycloalkyl, substituted or unsubstituted heterocycloalkyl, substituted or unsubstituted $C_1$–$C_6$-alkyl cycloalkyl, substituted or unsubstituted $C_1$–$C_6$-alkyl heterocycloalkyl, substituted or unsubstituted $C_1$–$C_6$-alkyl carboxy, acyl, substituted or unsubstituted $C_1$–$C_6$-alkyl acyl, substituted or unsubstituted $C_1$–$C_6$-alkyl acyloxy, substituted or unsubstituted $C_1$–$C_6$-alkyl alkoxy, alkoxycarbonyl, substituted or unsubstituted $C_1$–$C_6$-alkyl alkoxycarbonyl, aminocarbonyl, substituted or unsubstituted $C_1$–$C_6$-alkyl aminocarbonyl, substituted or unsubstituted $C_1$–$C_6$-alkyl acylamino, substituted or unsubstituted $C_1$–$C_6$-alkyl ureido, substituted or unsubsti-tuted $C_1$–$C_6$-alkyl amino, substituted or unsubstituted $C_1$–$C_6$-alkyl sulfonyloxy, sulfonyl, substituted or unsubstituted $C_1$–$C_6$-alkyl sulfonyl; sulfinyl, substituted or unsubstituted $C_1$–$C_6$-alkyl sulfinyl, substituted or unsubstituted $C_1$–$C_6$-alkyl sulfanyl and substituted or unsubstituted $C_1$–$C_6$-alkyl sulfonylamino.

$R^3$ in formula (I) is selected from the group consisting of substituted or unsubstituted aryl and substituted and unsubstituted heteroaryl.

X in formula (I) is selected from the group consisting of O or $NR^4$. Thereby, $R^4$ is selected from the group consisting of H, substituted or unsubstituted $C_1$–$C_6$-alkyl, substituted or unsubstituted aryl, substituted or unsubstituted heteroryl, substituted or unsubstituted $C_1$–$C_6$-alkyl aryl, substituted and unsubstituted $C_1$–$C_6$-alkyl heteroaryl. Preferably, $R^4$ is H or $C_1$–$C_6$-alkyl, like a methyl or ethyl group.

Alternatively, $R^2$ and $R^4$ in formula (I) may form—together with the N atom to which they are linked—a substituted or unsubstituted, 5–8 membered saturated or unsaturated heterocycloalkyl ring, e.g. a piperidinyl or piperazinyl moiety, which may be optionally fused with an aryl, heteroaryl, cycloalkyl or heterocycloalkyl ring.

n in formula (I) is an integer from 1 to 3, more preferred is 1 or 2.

In a second aspect, the present invention provides novel pyrrolidine derivatives of formula I for use as a medicament.

In a third aspect, the invention provides a pharmaceutical composition comprising a compound of formula I, together with a pharmaceutically acceptable excipient or carrier.

In a fourth aspect, the invention provides a compound of formula I, for the preparation of a pharmaceutical composition useful in the treatment and/or prevention of preterm labor, premature birth, dysmenorrhea.

In a fifth aspect, the invention provides a compound according to formula I for the modulation of the function of OT receptor.

In a sixth aspect, the invention provides a use of a compound of formula I for the treatment of a disease associated with the OT receptor such as preterm labor, premature birth, dysmenorrhea.

In a seventh aspect, the invention provides a method of treating a disease associated with the OT receptor such as preterm labor, premature birth, dysmenorrhea, comprising administering to a patient in need thereof an effective amount of a compound of formula I.

In an eighth aspect, the invention provides a method of synthesis of a compound according to formula I.

DETAILED DESCRIPTION OF THE INVENTION

It is an object of the present invention to provide substances which are suitable for the treatment and/or prevention of preterm labor, premature birth and dysmenorrhea.

It is notably an object of the present invention to provide chemical compounds which are able to down-regulate, including to antagonize, the function of OT in disease states in mammals, especially in humans.

It is also an object of the present invention to provide small molecule chemical compounds for the modulation, preferably the down-regulation or antagonization of the oxytocin receptor.

Moreover, it is an object of the present invention to provide methods for preparing said small molecule chemical compounds. It is furthermore an object of the present invention to provide a new category of pharmaceutical formulations for the treatment of preterm labor and dysmenorrhea, and/or diseases mediated by the oxytocin receptor.

It is finally an object of the present invention to provide a method for the treatment and/or prevention of disorders mediated by the oxytocin receptor, like preterm labor with oxytocin antagonists, acting for example by antagonizing the binding of oxytocin to its receptor.

The following paragraphs provide definitions of the various chemical moieties that make up the compounds according to the invention and are intended to apply uniformly throughout the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"$C_2$–$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"C$_2$–C$_6$-alkenyl aryl" refers to C$_2$–C$_6$-alkenyl groups having an aryl substituent, including 2-phenylvinyl and the like.

"C$_2$–C$_6$-alkenyl heteroaryl" refers to C$_2$–C$_6$-alkenyl groups having a heteroaryl substituent, including 2-(3-pyridinyl)vinyl and the like.

"C$_2$–C$_6$-alkynyl" refers to alkynyl groups preferably having from 2 to 6 carbon atoms and having at least 1–2 sites of alkynyl unsaturation, preferred alkynyl groups include ethynyl (—C≡CH), propargyl (—CH$_2$C≡CH), and the like.

"C$_2$–C$_6$-alkynyl aryl" refers to C$_2$–C$_6$-alkynyl groups having an aryl substituent, including phenylethynyl and the like.

"C$_2$–C$_6$-alkynyl heteroaryl" refers to C$_2$–C$_6$-alkynyl groups having a heteroaryl substituent, including 2-thienylethynyl and the like.

"C$_3$–C$_8$-cycloalkyl" refers to a saturated carbocyclic group of from 3 to 8 carbon atoms having a single ring (e.g., cyclohexyl) or multiple condensed rings (e.g., norborn yl). Preferred cycloalkyl include cyclopentyl, cyclohexyl, norbornyl and the like.

"Heterocycloalkyl" refers to a C$_3$–C$_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"C$_1$–C$_6$-alkyl cycloalkyl" refers to C$_1$–C$_6$-alkyl groups having a cycloalkyl substituent, including cyclohexylmethyl, cyclopentylpropyl, and the like.

"C$_1$–C$_6$-alkyl heterocycloalkyl" refers to C$_1$–C$_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"C$_1$–C$_6$-alkyl carboxy" refers to C$_1$–C$_5$-alkyl groups having an carboxy substituent, including 2-carboxyethyl and the like.

"Acyl" refers to the group —C(O)R where R includes "C$_1$–C$_6$-alkyl", "aryl", "heteroaryl", "C$_1$–C$_6$-alkyl aryl" or "C$_1$–C$_6$-alkyl heteroaryl".

"C$_1$–C$_6$-alkyl acyl" refers to C$_1$–C$_6$-alkyl groups having an acyl substituent, including 2-acetylethyl and the like.

"Acyloxy" refers to the group —OC(O)R where R includes "C$_1$–C$_6$-alkyl", "aryl", "heteroaryl", "C$_1$–C$_6$-alkyl aryl" or "C$_1$–C$_6$-alkyl heteroaryl".

"C$_1$–C$_6$-alkyl acyloxy" refers to C$_1$–C$_6$-alkyl groups having an acyloxy substituent, including 2-(acetyloxy)ethyl and the like.

"Alkoxy" refers to the group —O—R where R includes "C$_1$–C$_6$-alkyl" or "aryl" or "heteroaryl" or "C$_1$–C$_6$-alkyl aryl" or "C$_1$–C$_6$-alkyl heteroaryl". Preferred alkoxy groups include by way of example, methoxy, ethoxy, phenoxy and the like.

"C$_1$–C$_6$-alkyl alkoxy" refers to C$_1$–C$_5$-alkyl groups having an alkoxy substituent, including 2-ethoxyethyl and the like.

"Alkoxycarbonyl" refers to the group —C(O)OR where R includes H, "C$_1$–C$_6$-alkyl" or "aryl" or "heteroaryl" or "C$_1$–C$_6$-alkyl aryl" or "C$_1$–C$_6$-alkyl heteroaryl".

"C$_1$–C$_6$-alkyl alkoxycarbonyl" refers to C$_1$–C$_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or C$_1$–C$_6$-alkyl or aryl or heteroaryl or "C$_1$–C$_6$-alkyl aryl" or "C$_1$–C$_6$-alkyl heteroaryl".

"C$_1$–C$_6$-alkyl aminocarbonyl" refers to C$_1$–C$_6$-alkyl groups having an aminocarbonyl substituent, including 2-(dimethylaminocarbonyl)ethyl and the like.

"Acylamino" refers to the group —NRC(O)R' where each R, R' is independently hydrogen or "C$_1$–C$_6$-alkyl" or "aryl" or "heteroaryl" or "C$_1$–C$_6$-alkyl aryl" or "C$_1$–C$_6$-alkyl heteroaryl".

"C$_1$–C$_6$-alkyl acylamino" refers to C$_1$–C$_6$-alkyl groups having an acylamino substituent, including 2-(propionylamino)ethyl and the like.

"Ureido" refers to the group —NRC(O)NR'R" where each R, R', R" is independently hydrogen, "C$_1$–C$_6$-alkyl", "C$_2$–C$_6$-alkenyl", "C$_2$–C$_6$-alkynyl", "C$_3$–C$_8$-cycloalkyl", "heterocycloalkyl", "aryl", "heteroaryl", "C$_1$–C$_6$-alkyl aryl" or "C$_1$–C$_6$-alkyl heteroaryl", "C$_2$–C$_6$-alkenyl aryl", "C$_2$–C$_6$-alkenyl heteroaryl", "C$_2$–C$_6$-alkynyl aryl", "C$_2$–C$_6$-alkynylheteroaryl", "C$_1$–C$_6$-alkyl cycloalkyl", "C$_1$–C$_6$-alkyl heterocycloalkyl", and where R' and R", together with the nitrogen atom to which they are attached, can optionally form a 3–8-membered heterocycloalkyl ring.

"C$_1$–C$_6$-alkyl ureido" refers to C$_1$–C$_6$-alkyl groups having an ureido substituent, including 2-(N'-methylureido) ethyl and the like.

"Carbamate" refers to the group —NRC(O)OR' where each R, R' is independently hydrogen, "C$_1$–C$_6$-alkyl", "C$_2$–C$_6$-alkenyl", "C$_2$–C$_6$-alkynyl", "C$_3$–C$_8$-cycloalkyl", "heterocycloalkyl", "aryl", "heteroaryl", "C$_1$–C$_6$-alkyl aryl" or "C$_1$–C$_6$-alkyl heteroaryl", "C$_2$–C$_6$-alkenyl aryl", "C$_2$–C$_6$-alkenyl heteroaryl", "C$_2$–C$_6$-alkynyl aryl", "C$_2$–C$_6$-alkynylheteroaryl", "C$_1$–C$_6$-alkyl cycloalkyl", "C$_1$–C$_6$-alkyl heterocycloalkyl".

"Amino" refers to the group —NRR' where each R,R' is independently hydrogen or "C$_1$–C$_6$-alkyl" or "aryl" or "heteroaryl" or "C$_1$–C$_6$-alkyl aryl" or "C$_1$–C$_6$-alkyl heteroaryl", or "cycloalkyl", or "heterocycloalkyl", and where R and R', together with the nitrogen atom to which they are attached, can optionally form a 3–8-membered heterocycloalkyl ring.

"C$_1$–C$_6$-alkyl amino" refers to C$_1$–C$_5$-alkyl groups having an amino substituent, including 2-(1-pyrrolidinyl)ethyl and the like.

"Ammonium" refers to a positively charged group —N$^+$RR'R", where each R,R',R" is independently "C$_1$–C$_6$-alkyl" or "C$_1$–C$_6$-alkyl aryl" or "C$_1$–C$_6$-alkyl heteroaryl", or "cycloalkyl", or "heterocycloalkyl", and where R and R', together with the nitrogen atom to which they are attached, can optionally form a 3–8-membered heterocycloalkyl ring.

"Halogen" refers to fluoro, chloro, bromo and iodo atoms.

"Sulfonyloxy" refers to a group —OSO$_2$—R wherein R is selected from H, "C$_1$–C$_6$-alkyl", "C$_1$–C$_6$-alkyl" substituted with halogens, e.g., an —OSO$_2$—CF$_3$ group, "aryl", "heteroaryl", "(C$_1$–C$_6$-alkyl aryl" or "C$_1$–C$_6$-alkyl heteroaryl".

"C$_1$–C$_6$-alkyl sulfonyloxy" refers to C$_1$–C$_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "C$_1$–C$_6$-alkyl", "C$_1$–C$_6$-alkyl" substituted with halogens, e.g., an —SO$_2$—CF$_3$ group, "C$_1$–C$_6$-alkyl aryl" or "C$_1$–C$_6$-alkyl heteroaryl".

"C$_1$–C$_6$-alkyl sulfonyl" refers to C$_1$–C$_6$-alkyl groups having a sulfonyl substituent, including 2-(methylsulfonyl)ethyl and the like.

"Sulfinyl" refers to a group "—S(O)—R" wherein R is selected from H, "C$_1$–C$_6$-alkyl", "C$_1$–C$_6$-alkyl" substituted with halogens, e.g., an —SO—CF$_3$ group, "aryl", "heteroaryl", "C$_1$–C$_6$-alkyl aryl" or "C$_1$–C$_6$-alkyl heteroaryl".

"C$_1$–C$_6$-alkyl sulfinyl" refers to C$_1$–C$_6$-alkyl groups having a sulfinyl substituent, including 2-(methylsulfinyl)ethyl and the like.

"Sulfanyl" refers to groups —S—R where R includes "C$_1$–C$_6$-alkyl" or "aryl" or "hetero-aryl" or "C$_1$–C$_6$-alkyl aryl" or "C$_1$–C$_6$-alkyl heteroaryl". Preferred sulfanyl groups include methylsulfanyl, ethylsulfanyl, and the like.

"C$_1$–C$_6$-alkyl sulfanyl" refers to C$_1$–C$_6$-alkyl groups having a sulfanyl substituent, including 2-(ethylsulfanyl)ethyl and the like.

"Sulfonylamino" refers to a group —NRSO$_2$—R' where each R, R' is independently hydrogen or "C$_1$–C$_6$-alkyl" or "aryl" or "heteroaryl" or "C$_1$–C$_6$-alkyl aryl" or "C$_1$–C$_6$-alkyl heteroaryl".

"C$_1$–C$_6$-alkyl sulfonylamino" refers to C$_1$–C$_6$-alkyl groups having a sulfonylamino substituent, including 2-(ethylsulfonylamino)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C$_1$–C$_6$-alkyl", "C$_2$–C$_6$-alkenyl", "C$_2$–C$_6$-alkynyl", "cycloalkyl", "heterocycloalkyl", "C$_1$–C$_6$-alkyl aryl", "C$_1$–C$_6$-alkyl heteroaryl", "C$_1$–C$_6$-alkyl cycloalkyl", "C$_1$–C$_6$-alkyl heterocycloalkyl", "amino", "ammonium", "acyl", "acyloxy", "acylamino", "aminocarbonyl", "alkoxycarbonyl", "ureido", "carbamate," "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-specified compounds of formula (I). Examples of such salts include, but are not restricted, to base addition salts formed by reaction of compounds of formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step. "ee" is the percentage of excess of the major enantiomer vs minor enantiomer [% ee=% major–% minor]. In the absence of an asymmetric synthesis, racemic products are usually obtained that do however also have an activity as OT-R antagonists.

The term "preterm labor" or the term "premature labor" shall mean expulsion from the uterus of an infant before the normal end of gestation, or more particularly, onset of labor with effacement and dilation of the cervix before the 37$^{th}$ week of gestation. It may or may not be associated with vaginal bleeding or rupture of the membranes.

The term "dysmenorrhea" shall mean painful menstruation.

The term "caesarean delivery" shall mean incision through the abdominal and uterine walls for delivery of a foetus.

The present invention also includes the geometrical isomers, the optically active forms, enantiomers, diastereomers of compounds according to formula I, mixtures of these, racemates and also pharmaceutically acceptable salts.

The compounds according to the present invention are those of formula I.

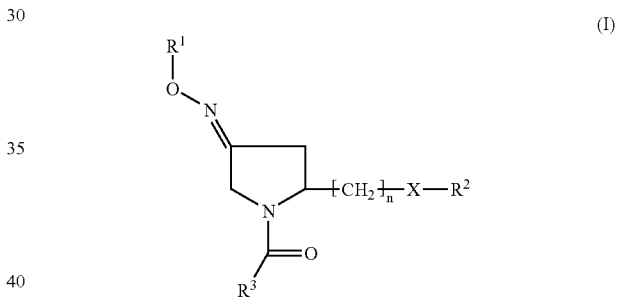

R$^1$ in formula (I) is selected from the group consisting of H and substituted or unsubstituted C$_1$–C$_6$-alkyl. Preferably R$^1$ is H or methyl.

R$^2$ in formula (I) is selected from the group consisting of hydrogen, substituted or unsubstituted C$_1$–C$_6$-alkyl, substituted or unsubstituted C$_1$–C$_6$-alkyl aryl, substituted or unsubstituted heteroaryl, substituted or unsubstituted C$_1$–C$_6$-alkyl heteroaryl, substituted or unsubstituted C$_2$–C$_6$-alkenyl, substituted or unsubstituted C$_2$–C$_6$-alkenyl aryl, substituted or unsubstituted C$_2$–C$_6$-alkenyl heteroaryl, substituted or unsubstituted C$_2$–C$_6$-alkynyl, substituted or unsubstituted C$_2$–C$_6$-alkynyl aryl, substituted or unsubstituted C$_2$–C$_6$-alkynyl heteroaryl, substituted or unsubstituted C$_3$–C$_8$-cycloalkyl, substituted or unsubstituted heterocycloalkyl, substituted or unsubstituted C$_1$–C$_6$-alkyl cycloalkyl, substituted or unsubstituted C$_1$–C$_6$-alkyl heterocycloalkyl, substituted or unsubstituted C$_1$–C$_6$-alkyl carboxy, acyl, substituted or unsubstituted C$_1$–C$_6$-alkyl acyl, substituted or unsubstituted C$_1$–C$_6$-alkyl acyloxy, substituted or unsubstituted C$_1$–C$_6$-alkyl alkoxy, alkoxycarbonyl, substituted or unsubstituted C$_1$–C$_6$-alkyl alkoxycarbonyl, aminocarbonyl, substituted or unsubstituted C$_1$–C$_6$-alkyl aminocarbonyl, substituted or unsubstituted C$_1$–C$_6$-alkyl acylamino, substituted or unsubstituted C$_1$–C$_6$-alkyl ureido, substituted or unsubsti-tuted C$_1$–C$_6$-alkyl amino, substituted or unsubstituted $C_1$–$C_6$-alkyl sulfonyloxy, sulfonyl, substituted or unsubstituted $C_1$–$C_6$-alkyl sulfonyl, sulfinyl, substituted or unsubstituted $C_1$–$C_6$-alkyl sulfinyl, substituted or unsubstituted $C_1$–$C_6$-alkyl sulfanyl, substituted and unsubstituted $C_1$–$C_6$-alkyl sulfonylamino.

$R^3$ in formula (I) is selected from the group consisting of substituted or unsubstituted aryl and substituted or unsubstituted heteroaryl.

X in formula (I) is selected from the group consisting of O or $NR^4$, wherein $R^4$ is selected from the group consisting of H, substituted or unsubstituted $C_1$–$C_6$-alkyl, substituted or unsubstituted aryl, substituted or unsubstituted heteroryl, substituted or unsubstituted $C_1$–$C_6$-alkyl aryl and substituted or unsubstituted $C_1$–$C_6$-alkyl heteroaryl. Preferably, $R^4$ is H or $C_1$–$C_6$-alkyl, like a methyl or ethyl group.

Alternatively, $R^2$ and $R^4$ in formula (I) may form—together with the N atom to which they are linked—a substituted or unsubstituted, 5–8 membered saturated or unsaturated heterocycloalkyl ring, e.g. a piperidinyl or piperazinyl moiety, which may be optionally fused with an aryl, heteroaryl, cycloalkyl or heterocycloalkyl ring.

n in formula (I) is an integer from 1 to 3, more preferred is 1 or 2.

Preferred $R^2$ in compounds according to formula I are those that are selected from the group consisting of H, acyl, preferably an acetyl moiety, an aryl, optionally substituted by a substituted or unsubstituted $C_1$–$C_6$-alkoxy, e.g. a methyloxy-phenyl goup, a $C_1$–$C_3$ alkyl like methyl or ethyl, optionally substituted by an substituted or unsubstituted acyl group or ester group, preferably formic acid or acetic acid t-butyl ester, N-(2-pyrrolidin-1-yl-ethyl)acetamide, and optionally substituted by an substituted or unsubstituted heteroaryl, preferably N-pyrazole.

Preferred $R^3$ in compounds according to formula I are those that are selected from the group consisting of aryl group optionally substituted by a substituted or unsubstituted aryl group. Particularly preferred $R^3$ is a biphenyl or 2-methyl biphenyl moiety.

A particularly preferred embodiment of the present invention is a pyrrolidine derivative according to formula I wherein X is O or NH and n is 1 or 2.

Another preferred embodiment of the present invention is a pyrrolidine derivative according to formula I wherein X is $NR^4$ and wherein $R^4$ and $R^2$ form a saturated or unsaturated, substituted or unsubstituted, fused or unfused, heterocyclic ring with the N atom they are linked to, preferably a 5 or 6-membered ring, more preferably a piperidine, a methylpiperazine or an isoindole-1,3-dione.

Compounds of formula I may be used for the treatment of a disease.

Specifically, the compounds of formula I are suitable for use in treating disorders such as preterm labor, premature birth, dysmenorrhea and for stopping labor prior to cesarean delivery. The compounds of the present invention are in particular useful for the treatment of preterm labor, premature birth and dysmenorrhea.

Preferably, the compounds according to Formula I alone or in a form of a pharmaceutical composition are suitable for the modulation of oxytocin function(s), thus specifically allowing the treatment and/or prevention of disorders which are mediated by the oxytocin receptor. Such modulation preferably involves the inhibition of OT-R function(s), notably by the antagonization of the oxytocin receptor in mammals, and in particular in humans.

Abnormal activity or hyperactivity of the oxytocin receptor are frequently involved in various disorders including the above enumerated disorders and disease states. Hence, the compounds according to the invention may be used for the treatment of disorders by modulating OT-R function or pathways. The modulation of the OT-R function or pathways may involve the down-regulation and/or inhibition of the oxytocin receptor. The compounds of the invention may be employed alone or in combination with further pharmaceutical agents, e.g. with a further OT-R modulator.

When employed as pharmaceuticals, the pyrrolidine derivatives of the present invention are typically administered in the form of a pharmaceutical composition. Hence, pharmaceutical compositions comprising a compound of Formula I and a pharmaceutically acceptable carrier, diluent or excipient are also within the scope of the present invention. A person skilled in the art is aware of a whole variety of such carriers, diluents or excipients suitable to formulate a pharmaceutical composition.

The compounds of the invention, together with a conventionally employed adjuvant, car-rier, diluent or excipient may be formulated as pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral adminis-tration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dio-xide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrrolidine derivatives of Formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of (6).

The compounds of this invention can also be administered in sustained release forms or from sustained release drug delivery systems. A description of representative sustained release materials can also be found in (6).

Still a further object of the present invention is a process for preparing pyrrolidine derivatives according to Formula I.

The pyrrolidine derivatives exemplified in this invention may be prepared from readily available or previously described starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Synthesis of Compounds of the Invention:

Examples of synthetic pathways for compounds of formula I will be described below.

The following abbreviations refer respectively to the definitions below:

ACN (Acetonitrile)
Boc (t-butoxycarbonyl)
$CDCl_3$ (deuterated chloroform)
cHex (Cyclohexane)
DCM (Dichloromethane)
DECP (Diethylcyanophosphonate)
DIC (Diisopropyl carbodiimide)
DIEA (disopropylethylamine)
DMAP (4- Dimethylaminopyridine)
DMF (Dimethylformamide)
DMSO (Dimethylsulfoxide)
DMSO-$d_6$ (deuterated dimethylsulfoxide)
EDC (1-(3-Dimethyl-amino-propyl)-3-ethylcarbodiimide)
EtOAc (Ethyl acetate)
$Et_2O$ (Diethyl ether)
HATU (O-(7-azabenzotriazol-1-yl-N,N,N',N'-tetramethyluroniumhexaflurophosphonate)
$K_2CO_3$ (potassium carbonate)
MEK (methylethylketone)
$MgSO_4$ (Magnesium sulfate)
NaH (Sodium hydride)
$NaHCO_3$ (Sodium bicarbonate)
nBuLi (n Butyllithium)
NMO (N-methylmorpholine N-oxide monohydrate)
PetEther (Petroleum ether)
OMs (O-mesylate=O-methylsulfonate)
OTs (O-tosylate=O-toluenesulfonate)
TBAF (t-butylammonium fluoride)
TBDMS (t-butyldimethylsilyl)
TBTU (O-Benzotriazolyl-N,N,N',N'-tetramethyluronium-tetrafluoroborate)
TEA (Triethyl amine)
TFA (Trifluoro-acetic acid)
THF (Tetrahydrofuran)
TPAP (tetrapropylammoniumperruthenate)
rt (room temperature).

a) Alkoxypyrrolidines:

Introduction of the $R^2$ Moiety

Alkoxypyrrolidine derivatives according to the general formula Ia (formula I wherein X is O), wherein $R^1$, $R^2$, $R^3$ and n are as defined for formula I, can be prepared from the corresponding pyrrolidine derivatives of formula II, wherein $R^1$, $R^3$ and n are as defined above. Alcohol derivatives of formula II are subjected to a direct O-alkylation by using a suitable alkylating agent $R^2$-LG, wherein LG is a suitable leaving group including Cl, Br, I or OMs, OTs. Alternatively, compounds Ia may be obtained by a Mitsunobu-type reaction as outlined in Scheme 1.

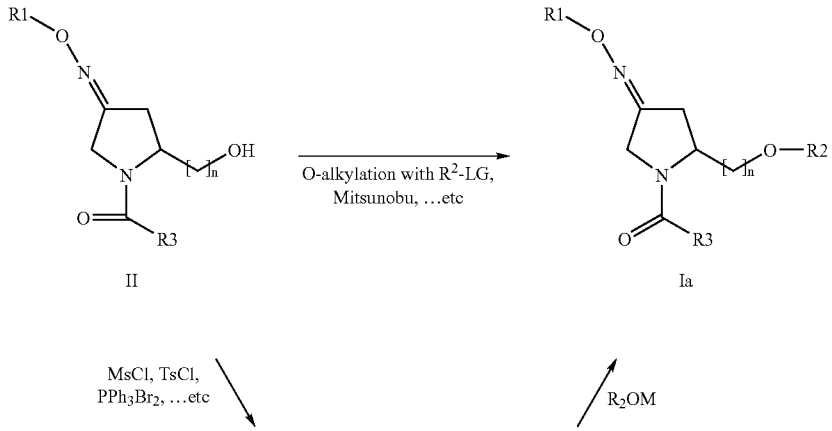

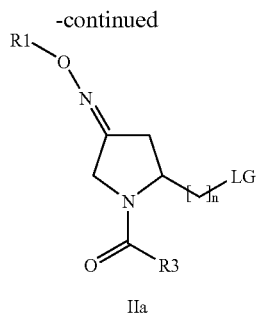

IIa

An alternative route for the synthesis of alkoxypyrrolidine derivatives according to the general formula Ia (formula I wherein X is O), can be the preparation of an intermediate of general formula IIa wherein $R^1$, $R^3$, n and LG are as defined above by reaction of an alcohol of formula II with MsCl, TsCl or a halogenating agent like $PPh_3Br_2$. The leaving group LG is then displaced by $R^2OM$ whereby $R^2$ is as above defined and M is H or a metal like Na to lead to compound of formula Ia.

Introduction of the Oxime Moiety

Compound of general formula II—whereby $R^1$, $R^3$ and n are as defined above—can be prepared from compounds of general formula IV wherein $R^3$ and n are as defined above and where $PG_1$ is a suitable alcohol protecting group, preferably a TBDMS. Ketone of general formula IV is reacted with a hydroxylamine derivative of general formula V wherein $R^1$ is as defined above. PG1 is removed via a deprotection step using standard synthetic techniques as shown in Scheme 2.

Scheme 2:

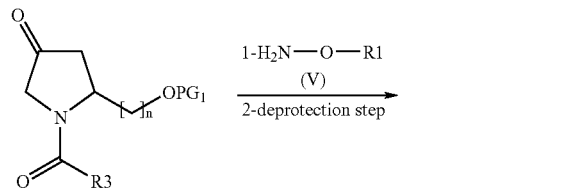

Hydroxylamine V, if not commercially available can, for example, be synthesized by reaction of N-Boc-hyroxylamine with the corresponding alkylating agent of formula VI whereby $R^1$ is as above defined and $X_a$=Cl, Br, I using standard conditions as outlined in Scheme 3.

Scheme 3:

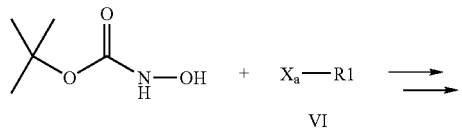

Formation of Ketopyrrolidines:

Ketopyrrolidines of general formula IV wherein $R^3$, n and $PG_1$ are as above defined can be obtained from the corresponding hydroxy pyrrolidine derivatives of formula VII wherein $R^3$, n and $PG_1$ are as above defined by treatment with appropriate oxidating agent e.g. DMSO/$(COCl)_2$/TEA (Swern conditions) or TPAP in the presence of NMO as illustrated in Scheme 4.

Scheme 4:

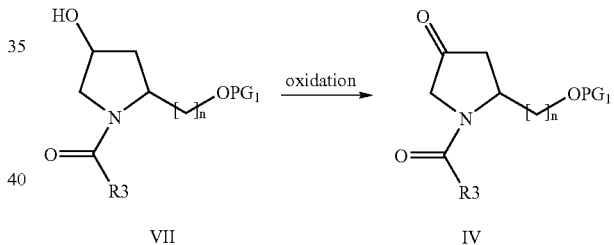

Reduction Step

Hydroxy pyrrolidine derivatives of general formula VII—wherein $R^3$ and n are as described above and $PG_1$ is a protecting group—may be obtained by reduction of the corresponding pyrrolidine carboxylic derivatives of formula VIII—wherein $R^3$ and n are as above defined, $R^7$ is H or an alkyl group and $PG_2$ is a suitable protecting group—after appropriate protection/deprotection steps as described in Scheme 5. A preferred reducing agent is $LiBH_4$ when $R^7$ is an alkyl group or LAH or $BH_3.DMS$ when $R^7$ is H.

Scheme 5:

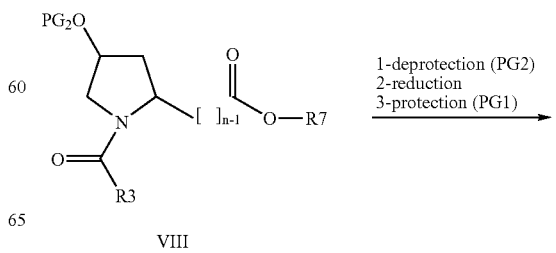

VIII

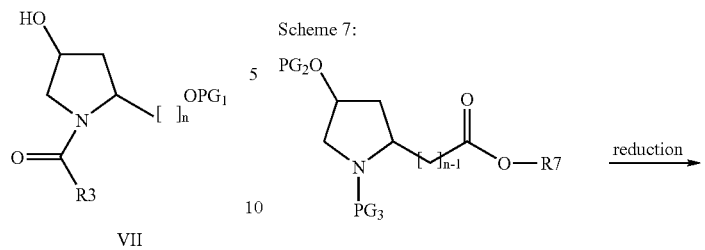

VII

Coupling Step

Protected pyrrolidines carboxylic derivatives of general formula VIII wherein $R^3$, n, $R^7$ and $PG_2$ are as above defined are prepared by reaction of a compound of general formula IX—wherein n, $R^7$ and $PG_2$ are as above defined and $PG_3$ is H or a suitable N-protecting group, preferably Boc—with an acylating agent of general formula $R^3$—CO—Y—wherein $R^3$ is as defined above and Y is any appropriate leaving group—as illustrated in Scheme 6.

Scheme 6:

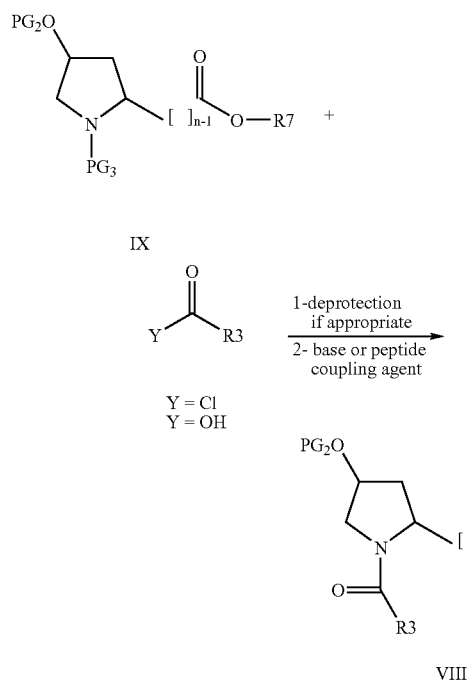

Preferred acylating agents are acid chlorides (Y=Cl) or carboxylic acids (Y=OH) used in conjunction with an appropriate peptide coupling agent such as e.g. DIC, EDC, HATU, DECP or others.

Generally, the starting materials are compounds of formula IX which can be obtained from commercial sources (e.g. protected 3-hydroxyproline, homo-3-hydroxyproline, 3-hydroxy pyrrolidine 5-propionic acid).

Other starting materials (such as compounds of formula XV, XVI, XIX and XX) can be obtained from commercially available compounds of formula IX via intermediates of formula XII.

In this case, first carboxylic derivatives of general formula IX can be reduced to derivatives of general formula XII whereby $PG_2$, $PG_3$, $R^7$ are as above defined and n=2 or 3 as described in Scheme 7.

Scheme 7:

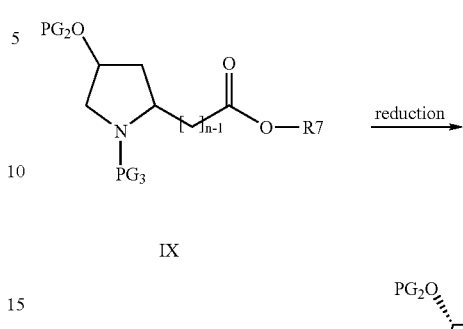

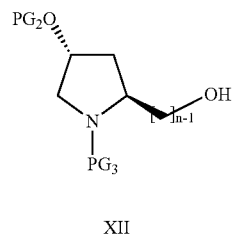

XII

Then, compounds of formula XII are subjected to classical protection/deprotection and functional group transformations, especially one or two carbons homologation procedures well known by the one skilled in the art (7, 8).

One preferred process consists in the homologation by one carbon of compounds of general formula XII wherein $PG_2$ and $PG_3$ are as above defined and n is 2 or 3 by displacement of a leaving group by a cyanide followed either by an hydrolysis to give carboxylic acids of general formula XV whereby $PG_2$, $PG_3$ and n are as above defined or a reduction to give amino compounds of general formula XVI whereby $PG_2$, $PG_3$ and n are as above defined as described in Scheme 8.

Scheme 8:

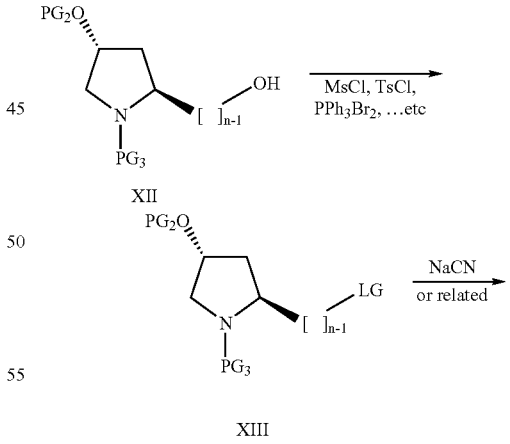

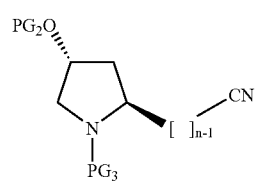

XIV

-continued

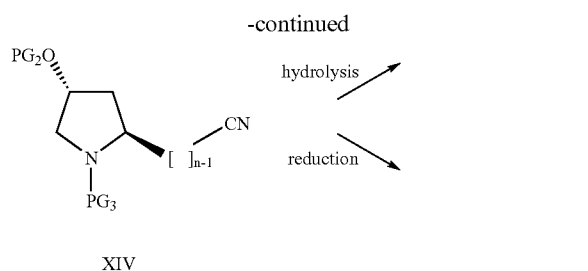

XIV

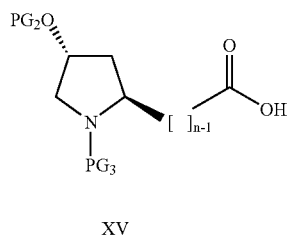

XV

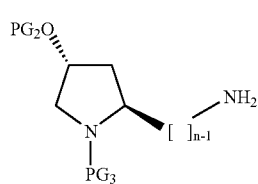

XVI

In case of a two-carbon homologation, one preferred procedure consists in reacting an aldehyde of general formula XVIII obtained by oxidation of a compound of general formula XII whereby $PG_2$, $PG_3$ and n are as above defined with a Wittig-Horner reagent as described in Scheme 9. The compound thus obtained is then reduced to compounds of general formula XIX whereby $PG_2$, $PG_3$, n and $R^7$ are as above defined.

Scheme 9:

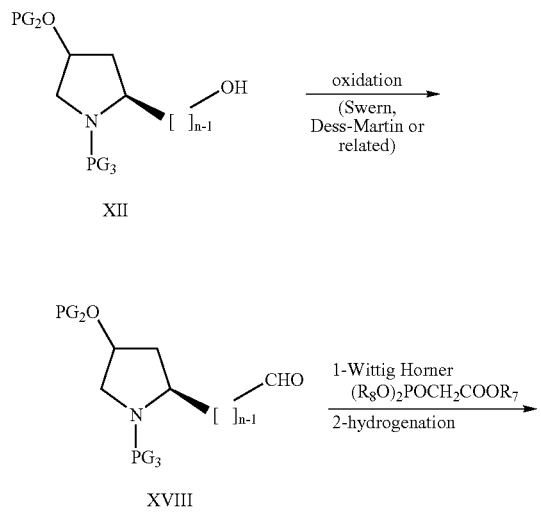

-continued

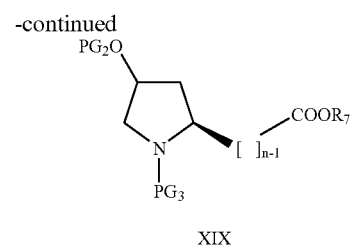

XIX

The four principal chemical transformations described above, i.e. the coupling step, the reduction step, the oxime formation and the introduction of the $R^2$ group can be performed in a different order. The most appropriate choice of the synthetic sequence will depend on the nature of the substituents $R^1$–$R^4$, n, X, and other parameters that can be appreciated by those skilled in the art.

b) Aminopyrrolidines:

Introduction of the $R^2$ Group:

Aminoalkylpyrrolidine derivatives according to the general formula Ib (formula I wherein X is $NR^4$), whereby $R^1$–$R^4$ and n are as defined in formula I, can be prepared from the corresponding pyrrolidine derivatives IIa obtained in a) from compounds of formula II according to scheme 1), wherein $R_1$, $R_3$, n and LG are as above defined by displacement of the LG group with the corresponding amine $HNR^2R^4$, as outlined is Scheme 10.

Scheme 10:

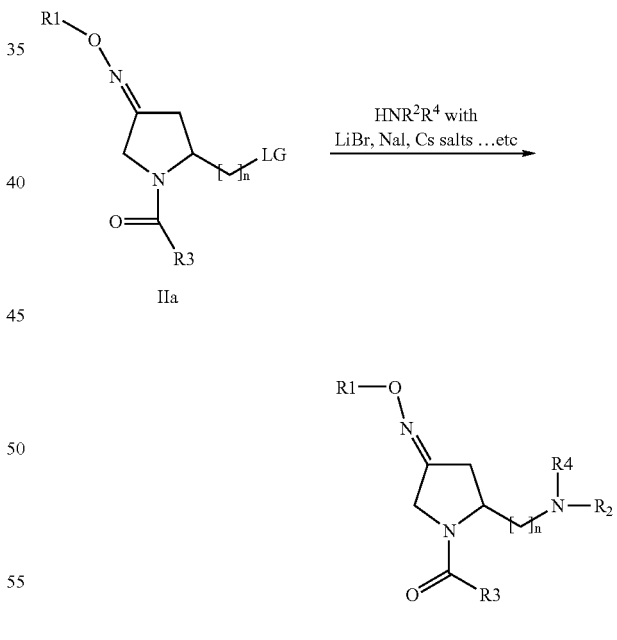

An alternative way for the preparation of aminoalkylpyrrolidine derivatives according to general formula Ib (formula I wherein X is $NR^4$) wherein $R^1$–$R^4$ and n are as defined above is described in Scheme 11. According to such process, the hydroxy moiety in the pyrrolidine derivatives of general formula II (that can be obtained from compounds of formula IV; see scheme 2) wherein $R^1$, $R^3$ and n are as above defined is oxidized into the corresponding aldehyde using well known conditions for such transformation, e.g. DMSO/(COCl)$_2$, TEA (Swern conditions) or Dess Martin reagent. The aldehyde is then reacted with amines HNR$^2$R$^4$ whereby R$^2$ and R$^4$ are as above defined under reducing conditions.

Scheme 11:

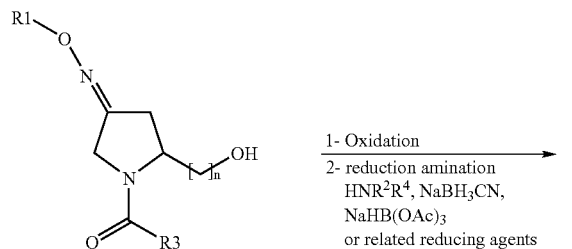

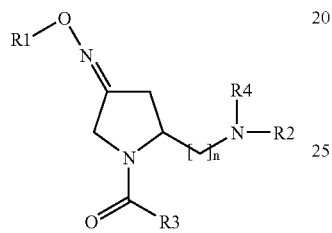

In the case of aminoalkylpyrrolidine derivatives according to general formula Ib wherein R$^4$ is H and R$^1$, R$^2$, R$^3$ and n are as defined above, an alternative synthetic approach may be adopted. Aminoalkylpyrrolidine derivatives according to general formula Ib (formula I wherein X is NH) can then be obtained from the corresponding aminoalkylpyrrolidine derivatives of formula III wherein R$^1$, R$^3$ and n are as defined above by direct alkylation with R$^2$-LG wherein R$^2$ and LG are as above defined or reductive alkylation with aldehyde of the formula R$^2$CHO—wherein R$^2$ is as defined above—and using an appropriate reducing agent as illustrated in Scheme 12.

Scheme 12:

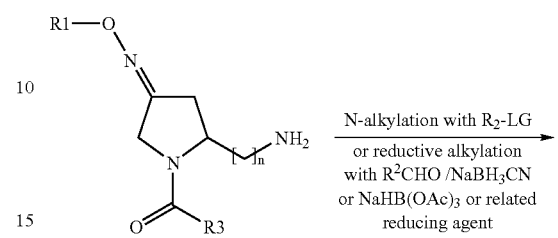

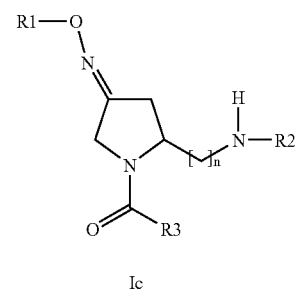

Aminoalkyl derivatives of formula III wherein R$^1$, R$^3$ and n are as above defined can be obtained from hydroxyalkylpyrrolidine of formula II (which can be obtained from compounds of formula IV; see scheme 2) wherein R$^1$, R$^3$ and n are as defined above or derivatives of general formula IIa (which can be obtained from compounds of formula II according to scheme 1) wherein R$^1$, R$^3$, n and LG are as above defined by well known procedures for such functional group transformations. Two examples of such transformations are illustrated in Scheme 13.

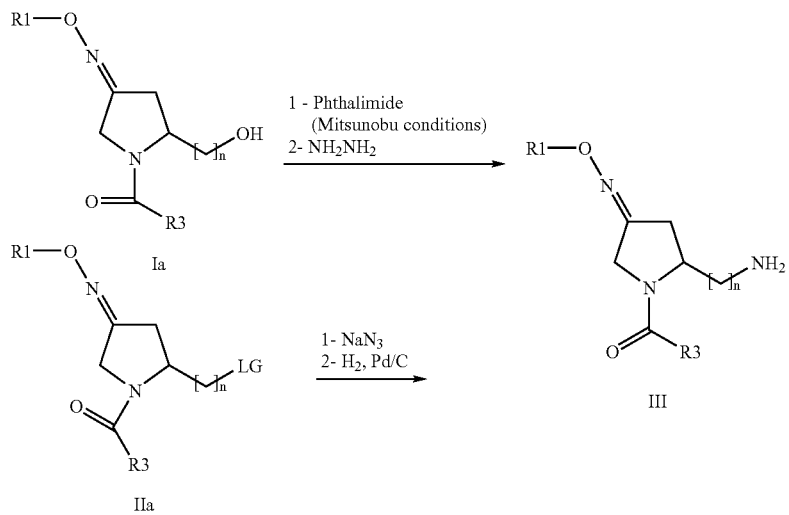

For compounds of formula Ib (formula I wherein X is $NR^4$) wherein $R^2$ is $COR^5$, $SO_2R^5$, $COOR^5$, $CONR^5R^6$, $SO_2NR^5R^6$ whereby $R^5$ and $R^6$ are substituted or unsubstituted alkyl or aryl group and $R^4$ is H or a substituted or unsubstituted alkyl or aryl group, the methods described above in Scheme 10, 11 and 12 are not applicable.

In this case these compounds of formula Ib can then be obtained by treatment of a compound of general formula Ic (compound of formula Ib wherein $R^2$ is H obtained according to methods set out in Schemes 10, 11 or 12 with a suitable acylating agent, including acylchlorid or a carboxylic acid in conjunction with a peptide coupling agent, e.g. DIC or EDC, a sulfonating agent and others as outlined in Scheme 14.

Scheme 14:

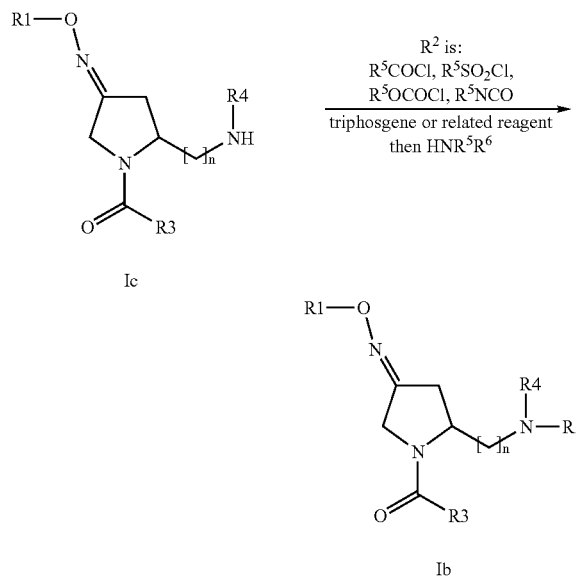

The other steps, i.e. introduction of the oxime moiety, formation of ketopyrrolidines, reduction step and coupling step, have already been described in the above item a).

However, like for the synthesis of alkoxypyrrolidines, the four principal chemical transformations described above, can be performed in a different order. The most appropriate choice of the synthetic sequence will depend on the nature of the substituents $R^1$–$R^4$, n, X, and other parameters that can be appreciated by those skilled in the art.

As an example, compounds of general formula I whereby $R^1$–$R^4$, n and X are as above defined can be obtained from ketopyrrolidine of general formula X whereby $R^2$, $R^3$, n and X are as defined above by reaction with a hydroxylamine V whereby $R_1$ is as above defined as described in Scheme 15, which leads to the introduction of the oxime moiety.

Scheme 15:

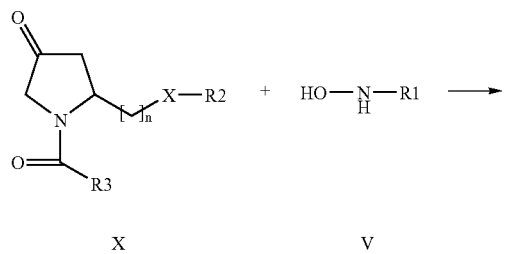

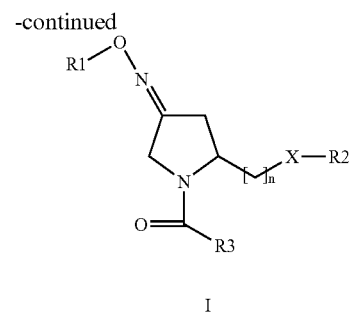

The ketopyrrolidine of formula X can be obtained by oxidation of an alcohol of general formula XI whereby $R^2$, $R^3$, n and X are as defined above and $PG_2$ is H or a suitable O-protecting group under similar conditions as for the transformation of compounds of general formula VII in compounds of general formula IV as described in Scheme 16.

Scheme 16:

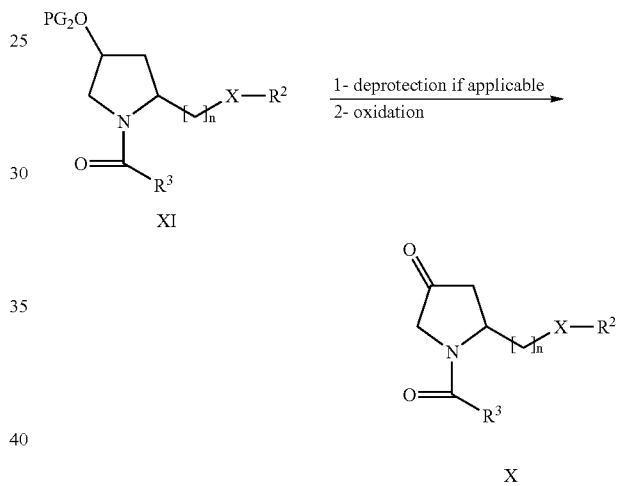

Compounds of general formula XI wherein $R^2$, $R^3$, n, $PG_2$ and X are as defined above can be obtained from compounds of general formula VII, wherein $R^3$, n and PG1 are as above defined by the introduction of the $R^2$ group following one of the processes described in Schemes 1, 10, 11, 12, 13 or 14. The choice of the process will depend on the nature of $R^3$, $R^2$, n and X and will be appreciated by those skilled in the art as well as the choice and sequence of appropriate protection/deprotection steps as described in Scheme 17.

Scheme 17:

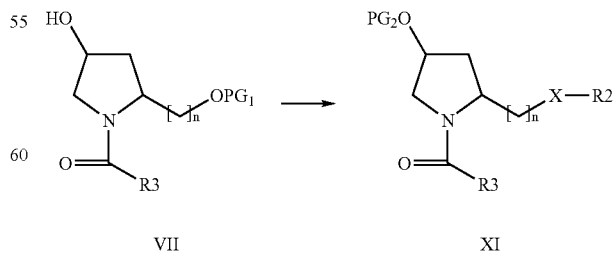

The obtention of compounds of formula VII, like the reduction step has been already described above.

The reaction sequences outlined in the above Schemes provide enantiomerically pure compounds of formula I, if enantiomerically pure starting materials are used. (R)- as well as (S)-enantiomers can be obtained depending upon whether (R)- or (S)-forms of commercially available compounds of formulas IX were used as the starting materials.

The reaction sequences outlined in the above reaction schemes usually provide mixtures of (E)- and (Z)-isomers with respect to the substituents on the exocyclic double bond of the pyrrolidine ring. (E)/(Z)-isomers could be separated by standard chromatography techniques well known to the person skilled in the art, such as by reversed phase high-pressure liquid chromatography (HPLC) or silica gel flash chromatography (FC). Alternatively, either one of the (E)/(Z)isomers could successively be enriched by selective crystallisation in appropriate solvents or solvent mixtures. The assignment of the absolute configuration of the exocyclic double bond was performed using NMR-techniques well described in the literature as will be known to the practitioner skilled in the art (for configuration assignments of e.g. oxime functionalities (9). In order to increase the overall yields of one isomer (usually the (Z)-isomer), the other isomer (usually the (E)-isomer) could be recycled by deliberate re-isomerization in organic solvents containing traces of acid, such as HCl, followed again by (E)/(Z)-separation through chromatography and /or crystallisation.

According to a further general process (scheme 18), compounds of formula I can be converted to alternative compounds of formula I, employing suitable interconversion techniques such as hereinafter described in the Examples.

If the above set out general synthetic methods are not applicable for obtaining compounds according to formula I and/or necessary intermediates for the synthesis of compounds of formula I, suitable methods of preparation known by a person skilled on the art should be used. In general, the synthesis pathways for any individual compound of formula I will depend on the specific substitutents of each molecule and upon the ready availability of intermediates necessary; again such factors being appreciated by those of ordinary skill in the art. For all the protection, deprotection methods, see (7, 10).

EXAMPLES

The invention will be illustrated by means of the following examples which are not to be construed as limiting the scope of the invention.

The compounds of the present invention may be synthesized according to the different synthesis pathways provided above. The following examples illustrate preferred methods for synthesizing the compounds according to formula I, and for determining their biological activities.

Example I (3EZ,5S)-5-(hydroxymethyl)-1-[(2'-methyl-1,1'-biphenyl-4yl) carbonyl] pyrrolidin-3-one O-methyloxime (1) (Compound of Formula II or Formula Ia wherein $R^2$ is H)

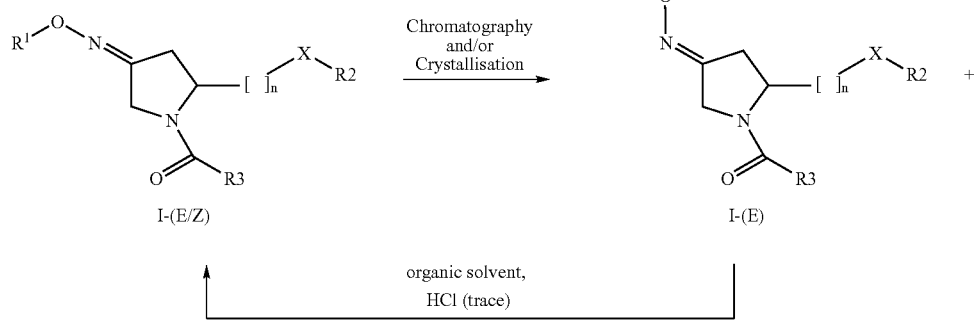

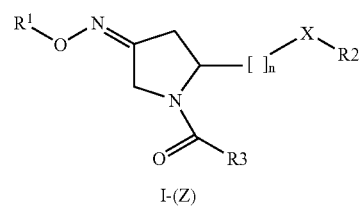

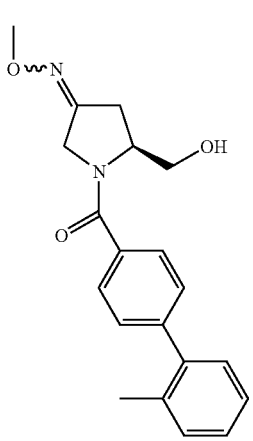

(1)

Intermediate (1a): 1-(tert-butoxycarbonyl)-4-oxo-L-proline

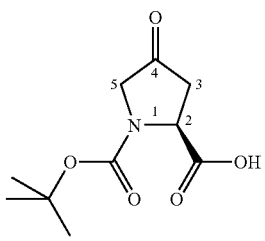

(1a)

Ketopyrrolidine Formation:

Commercial (2S, 4R)-1-(tert-butoxycarbonyl)-4-hydroxy-2-pyrrolidinecarboxylic acid (30 g, 0.13 mol) was dissolved in acetone (1500 ml). A mechanical stirrer was placed in the flask and the solution stirred vigorously. A freshly made solution of 8N chromic acid was prepared by dissolving chromium trioxide (66.7 g, 0.667 mol) in water (40 ml), adding concentrated sulphuric acid (53.3 ml) and adding enough water to bring the solution volume to 115 ml. The 8N chromic acid solution (115 ml) was then added dropwise over a period of 30 min with continued vigorous stirring, the reaction's exotherm being maintained at the optimal temperature of 25° C. by the use of an ice bath. After the complete addition of the chromic acid, the reaction mixture was stirred for a further 15 minutes—maintaining the optimal temperature of 25° C. The reaction mixture was then quenched by the addition of methanol (20 ml). Exotherm was controlled by the use of an ice bath and, if necessary, direct addition of a small amount of crushed ice to the reaction mixture itself. The reaction mixture was filtered through a Celite pad and then concentrated in vacuo. The resulting acidic solution was then extracted with ethyl acetate (3×300 ml) and the combined organic layers washed with brine (2×100 ml), then dried with magnesium sulfate and concentrated in vacuo. The crude product was recrystallized from ethyl acetate to give a white crystalline product, (2S)-1-(tert-butoxycarbonyl)-4-oxo-2-pyrrolidinecarboxylic acid (22.55 g, 76%) (1a). (1H NMR (360 MHz, CDCl3): 1.4 (m, 9H), 2.5–3.0 (m, 2H), 3.7–3.9 (m, 2H), 4.75 (dd, 1H)).

Intermediate 1b: (4EZ)-1-(tert-butoxycarbonyl)-4-(methoxyimino)-L-proline

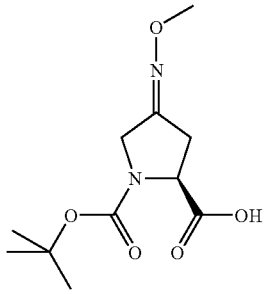

(1b)

Introduction of the Oxime Moiety:

A solution was made containing (2S)-1-(tert-butoxycarbonyl)-4-oxo-2-pyrrolidine-carboxylic acid (Intermediate 1a, 5.0 g, 21 mmol) and O-methylhydroxylamine hydrochloride (2.7 g, 32.8 mmol) in chloroform (100 ml) containing triethylamine (5.5 g, 55 mmol). The reaction mixture was then stirred at ambient temperature overnight, prior to removal of solvent. The resultant crude reaction mixture was dissolved in ethyl acetate (150 ml) and washed rapidly with 1N HCl (40 ml). The acidic layer was then extracted with ethyl acetate (3×20 ml) and the combined organic layers washed with brine before drying over magnesium sulfate, filtering and removal of solvent in vacuo. The desired product (1b) (5.3 g, 94%) was isolated as a pale yellow oil. $^1$H NMR (400 MHz, CDCl$_3$); 1.45 (m, 9H), 2.8–3.2 (m, 2H), 3.9 (s, 3H), 4.2 (m, 2H), 4.5–4.7 (m, 1H).

Intermediate 1c: 1-tert-butyl-2-methyl (2S,4EZ)-4-(methoxyimino)pyrrolidine-1,2-dicarboxylate.

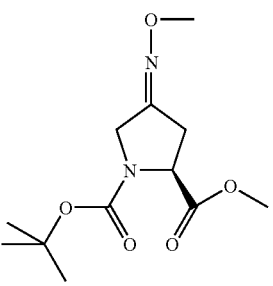

(1c)

A solution of the oximether (2S,4EZ)-1-(tert-butoxycarbonyl)-4-(methoxyimino)-2-pyrrolidinecarboxylic acid (intermediate 1b, 0.648 g, 2.5 mmol), in a 1:1 mixture of methanol and toluene (35 ml) was made. Trimethylsilyl diazomethane (3.8 ml of a 2M solution in hexanes, 7.5 mmol) was then added dropwise to the stirred solution at room temperature under nitrogen. After completion of the evolution of nitrogen gas, the resulting yellow solution was evaporated in vacuo, and the residue filtered through a pad of silica gel, eluting with ethyl acetate. Removal of solvent from the filtrate gave the methylester (1c) product as a yellow oil (0.646 g, 95% yield).

Intermediate 1d: Methyl (2S,4EZ)-4-(methoxyimino)-1-[(2'-methyl[1,1'-biphenyl]-4-yl)carbonyl]-2-pyrrolidinecarboxylate.

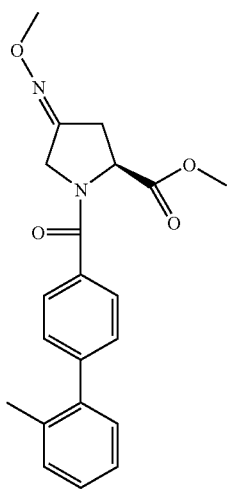

(1d)

Coupling the R³ Moitey:

A solution was made containing 1-tert-butyl-2-methyl (2S,4EZ)-4-(methoxyimino)-1,2-pyrrolidine-dicarboxylate (intermediate 1c, 0.892 g, 3.28 mmol) in anhydrous DCM (28 ml). TFA (20%, 7 mL) was added drop wise. The mixture was stirred at r.t. for 20 min. Solvents were evaporated and the desired product, (0.564 g, quant.) was isolated as a yellow oil. It was directly dissolved in a 7:3 mixture of DCM and DMF (30 ml) and treated with 2'-methyl[1,1'-biphenyl]-4-carboxylic acid (0.765 g, 3.60 mmol) and 4-dimethylaminopyridine (0.880 g, 7.21 mmol). EDC (0.691 mg, 3.60 mmol) was added slowly at 0° C. and the reaction mixture was stirred overnight at rt. It was washed with water (twice 20 ml), dried over MgSO₄, filtrated and evaporated in vacuo.

Intermediate 1e: (2 S,4EZ)-4-(methoxyimino)-1-[(2'-methyl[1,1'-biphenyl]-4-yl)carbonyl]-2-pyrrolidinecarboxylic acid.

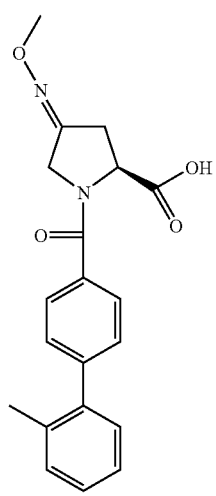

(1e)

Introduction of the R₂ Moiety:

Methyl(2S,4EZ)-4-(methoxyimino)-1-[(2'-methyl[1,1'-biphenyl]-4-yl)carbonyl]-2-pyrrolidinecarboxylate (intermediate 1d, 391 mg, 1.06 mmol) was stirred at rt for 4 h in a solution containing dioxan (9 ml), water (3 ml) and NaOH (1.13 ml of a 1.6 N solution). Dioxan was removed in vacuo and the solution was made acidic by treatment with HCl 0.1 N. It was extracted with EtOAc, washed with brine, dried over magnesium sulfate, filtered and concentrated to give the desired product (1e) (342 mg, yield=91%). 1H NMR (300 MHz, CDCl3): 2.23 (s, 1.5H), 2.25 (s, 1.5H), 3.10 (m, 2H), 3.83 (s, 1.5H), 3.85 (s, 1.5H), 4.10 (m, 2H), 5.18 (m, 1H), 7.18 (m, 4H), 7.37 (m, 2H), 7.57 (m, 2H).

MS (APCI+): 353 (M+1) (APCI−): 351 (M+1).

Example I: (2S,4EZ)-4-(methoxyimino)-1-[(2'-methyl[1,1'-biphenyl]-4-yl)carbonyl]-2-pyrrolidinecarboxylic acid (intermediate 1e, 50 mg, 0.14 mmol) was dissolved in THF (1 ml) and treated with ethylchloroformate (163 μl, 0.17 mmol) and TEA (29 μl, 0.76 mmol) at −15° C. The reaction mixture was stirred at this temperature and under nitrogen atmosphere for 30 mn before the addition of sodium borohydride (13.4 mg in 0.65 ml water, 0.35 mmol). It was then allowed to warm to rt. After 3 h, the reaction was quenched with 2.5 ml of a 1 N HCl solution, and extracted with EtOAc three times. The combined organic layers were washed with a 0.1N HCl solution (three times), water (three times), dried over magnesium sulfate, filtered and concentrated to give compound (1).

Yield: 12% (6 mg)
Appearance: yellow oil
MS (APCI+): 339 (M+1)
HPLC purity: 90.1%

Example II (3EZ,5S-1-(1,1'-biphenyl-4-ylcarbonyl)-5 (hydroxymethyl) pyrrolidin-3-one O-methyloxime (2),
(3Z,5S)-1-(1,1'-biphenyl-4-ylcarbonyl)-5 (hydroxymethyl)pyrrolidin-3-one O-methyloxime (3),
(3E,5S)-1-(1,1'-biphenyl-4-ylcarbonyl)-5-(hydroxymethyl) pyrrolidin-3-one O-methyloxime (4)
(Compounds of Formula II or Ia wherein R² is H)

Intermediate 2a: methyl (4R)-1-(1,1'-biphenyl-4-ylcarbonyl)-4-hydroxy-L-prolinate (Compound of Formula VIII).

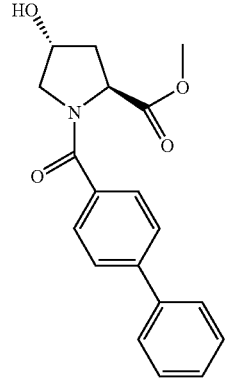

(2a)

To a solution of 4-biphenylcarboxylic acid (17.5 g, 88.3 mmol) in DMF (100 ml) were added EDC (16.9 g, 88.3 mmol), HOBt (11.9 g, 88.3 mmol) and DIEA (27.9 ml, 183.9 mmol). The mixture was then stirred at r.t. for 10 mn before the addition of trans-hydroxy-L-proline methylester hydrochloride (10.7 g, 73.6 mmol) and left for another 48 h at r.t. under nitrogen atmosphere. It was then concentrated under high vacuum and dissolved in Ethyl acetate, washed with water, 1N chlorhydric acid solution, saturated sodium hydrogenocarbonate solution and brine. It was finally dried over magnesium sulfate, filtered and concentrated. The crude thus obtained was purified by flash-chromatography with cyclohexane/ethyl acetate 90:10 (compound 2a).

Yield: 53% (12.6 g)

Appearance: brown solid

1H NMR (CDCl3): 2.11 (m, 1H), 2.36 (m, 1H), 3.58 (d, J=11.5 Hz, 1H), 3.77 (s, 3H), 3.86 (dd, J=3.4 and 11.1 Hz, 1H), 4.51 (s, 1H), 4.86 (t, J=8.3 Hz, 1H), 7.33–7.62 (m, 9H).

MS (APCI+): 651 (2M+1).

Intermediate 2b: (3R,5S)-1-(1,1'-biphenyl-4-ylcarbonyl)-5-(hydroxymethyl)-pyrrolidin-3-ol.

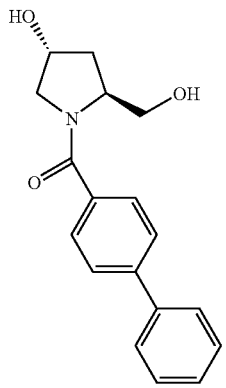

(2b)

Lithium borohydride (600 mg, 25.8 mmmmol) was slowly added to a solution of methyl ester (2a) (5.6 g, 17.2 mmol) in THF (80 mL) at 0° C. under nitrogen atmosphere. The mixture was stirred at r.t. for 2h and the borohydride neutralized with water. The white precipitate containing compound (2b) was filtered and washed with ether.

Yield: 82% (4.2 g)

Appearance: white solid

1H NMR (DMSO): 1.90–2.02 (m, 2H), 3.24–3.30 (m, 2H), 3.57 (m, 2H), 3.67 (m, 1H), 4.18 (m, 1H), 4.28 (m, 1H), 4.80 (brs, 1H), 7.39–7.74 (m, 9H). APCI (+): 299 (M+1)

Intermediate 2c: (3R,5S)-1-(1,1'-biphenyl-4-ylcarbonyl)-5-({[tert-butyl (dimethyl) silyl]oxy}methyl)pyrrolidin-3-ol (Compound of Formula VII).

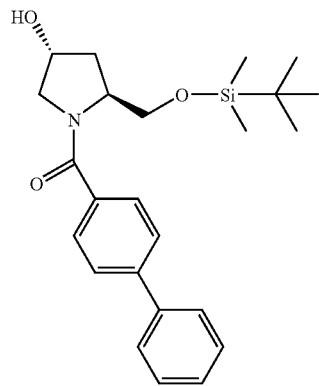

(2c)

A solution of diol (2b) (4.2 g, 14.1 mmol) and TBDMS-Cl (1.9 g, 12.6 mmol) in DMF (40 ml) was diluted with DCM (150 ml) and treated with DBU (421 µl, 2.81 mmol) and TEA (1.96 ml, 14.1 mmol). The reaction mixture was then allowed to stir for 16 h at r.t. under nitrogen atmosphere. After dilution with ethyl acetate, the organic phase was washed with water. Aqueous phase was extracted again with ethyl acetate and the combined organic phases were washed with saturated ammonium chlorid solution and three times with brine before being dried over magnesium sulfate, filtered and concentrated. The crude thus obtained was purified by flash chromatography with DCM/MeOH 95:5 (compound 2c).

Yield: 75% (4.39 g)

Appearance: white powder

1H NMR (DMSO): 0.03 (s, 6H), 0.88 (s, 9H), 1.92–2.04 (m, 2H), 3.30 (m, 1H), 3.54 (m, 1H), 3.72 (brd, J=9.0 Hz, 1H), 3.92 (m, 1H), 4.20 (m, 1H), 4.30 (m, 1H), 4.83 (m, 1H), 7.37–7.56 (m, 5H), 7.77 (m, 4H).

LC/MS (ESI, +): 412 (M+1).

Intermediate 2d: (5S)-1-(1,1'-biphenyl-4-ylcarbonyl)-5-({[tert-butyl (dimethyl) silyl]oxy}methyl)pyrrolidin-3-one (Compound of Formula IV).

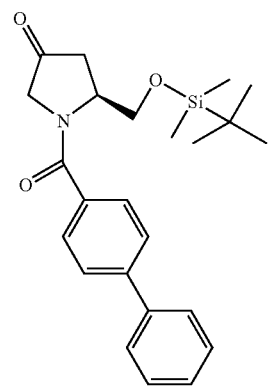

(2d)

A solution of dry DMSO (2.04 ml, 28.8 mmol) in DCM (15 ml) was slowly added to a solution of oxalyl chlorid (1.34 ml, 15.7 mmol) in DCM (5 mL) at −78° C. under nitrogen atmosphere. The mixture was allowed to stir for 30 mn before the slow addition of alcohol (2c) (5.38 g, 13.1 mmmol) in DCM (50 ml). The reaction mixture was stirred for 3 h at −78° C., treated dropwise with TEA (9.06 ml, 65.3 mmol) and allow to warm to r.t. It was then washed with brine, 1N HCl solution, with brine again, dried over magnesium sulfate, filtered and concentrated Compound 2d.

Yield: 91% (4.88 g)

Appearance: brown oil

1H NMR (CDCl3): 0.06 (s, 6H), 0.86 (s, 9H), 2.49–2.70 (m, 2H), 3.69 (m, 1H), 3.84 (m, 1H), 3.98 (m, 1H), 4.20 (m, 1H), 5.07 (m, 1H), 7.37–7.65 (m, 9H).

LC/MS (ESI,+): 410 (M+1).

Intermediate 2e: (3EZ,5S)-1-(1,1'-biphenyl-4-ylcarbonyl)-5-({[tert-butyl (dimethyl) silyl]oxy}methyl)pyrrolidin-3-one O-methyloxime.

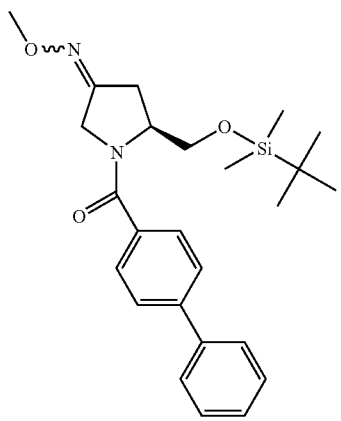

(2e)

A mixture of ketone 2d (4.78 g, 11.7 mmol), methylhydroxylamine hydrochlorid (2.44 g, 29.2 mmol) and TEA (4.05 ml, 29.2 mmol) in chloroform (80 ml) is heated at 65° C. for 16 h. The mixture is then washed with brine, 1N HCl solution, brine again and dried over magnesium sulfate, filtered and concentrated to give compound 2e.

Yield: 86% (4.41 g)

Appearance: brown oil

1H NMR (CDCl3): 0.06 (s, 6H), 0.88 (s, 9H), 2.68–2.90 (m, 2H), 3.42 (m, 1H), 3.78 (s, 1.5H), 3.83 (s, 1.5H), 4.1 (m, 2H), 4.31 (m, 1H), 4.83 (m, 1H), 7.34–7.64 (m, 9H).

LC/MS: ESI (+): 439 (M+1)

Final Compounds: (3EZ,5S)-1-(1,1'-biphenyl-4-ylcarbonyl)-5 (hydroxymethyl) pyrrolidin-3-one O-methyloxime (2), (3Z,5S)-1-(1,1'-biphenyl-4-ylcarbonyl)-5 (hydroxymethyl)pyrrolidin-3-one O-methyloxime (3), (3E,5S)-1-(1,1'-biphenyl-4-ylcarbonyl)-5-(hydroxymethyl)pyrrolidin-3-one O-methyloxime (4) (compounds of formula II or of formula Ia when $R^2$ is H):

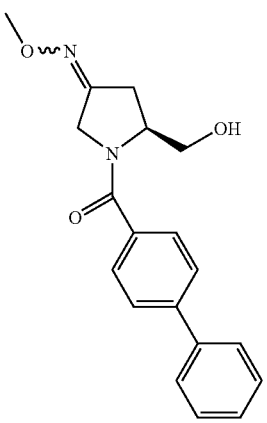

(2)

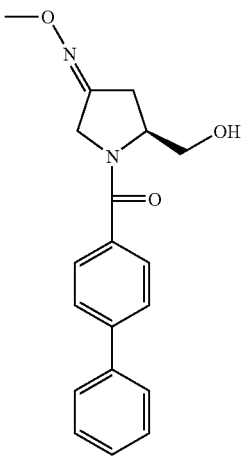

(3)

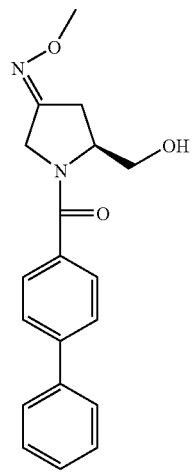

(4)

A solution of TBAF (14.1 ml of a solution 1M in THF, 14.1 mmol) was added to a solution of oxime (2e) (4.13 g, 9.41 mmol) in THF (100 ml). The reaction mixture was allowed to stir at room temperature overnight. It was then concentrated and diluted with ethyl acetate. Organic phase was washed with water, 1H HCl solution and brine before being dried over magnesium sulfate, filtered and concentrated.

Yield: quantitative of the EZ mixture (2)
Appearance: white foam
LC/MS: ESI (+): 325 (M+1)

The two isomers E and Z were separated by flash chromatography using ethyl acetate/cyclohexane 80:20 as eluant.

Less polar fraction: (3E,5S)-1-(1,1'-biphenyl-4-ylcarbonyl)-5-(hydroxymethyl) pyrrolidin-3-one O-methyloxime (3)
Rf: 0.36 (AcOEt/cyclohexane 80:20)
Yield: 25% (765 mg)
Appearance: white foam
1H NMR (DMSO): 2.64 (brs, 2H), 3.20–3.7 (m, 3H), 3.80 (s, 3H), 3.8–4.6 (m, 2H), 5.00 (t, J=8.0 Hz, 1H), 7.37–7.60 (m, 9H).

IR (film): 3292, 1604, 1417, 1040

MS(APCI,+): 325 (M+1)

Elemental analysis: (C$_{19}$H$_{20}$N$_2$O$_3$;0.2H$_2$O): calc.: C: 69.58; H: 6.27; N: 8.54; exp.: C: 69.53; H: 6.32; N: 8.36

HPLC purity: 98.6%

More polar fraction: (3Z,5S)-1-(1,1'-biphenyl-4-ylcarbonyl)-5-(hydroxymethyl) pyrrolidin-3-one O-methyloxime (4)

Rf: 0.22 (AcOEt/cyclohexane 80:20)

Yield: 33% (1013 mg)

Appearance: white powder

Melting point: 189° C.

1H NMR (DMSO): 2.64–2.82 (m, 2H), 3.20–3.57 (m, 3H), 3.70–3.80 (m, 3H), 3.98–4.60 (m, 2H), 5.0 (t, J=8.0 Hz, 1H), 7.37–7.76 (m, 9H).

IR (film): 3373, 1606, 1417, 1045

MS (APCI,+): 649 (2M+1), 325 (M+1)

Elemental analysis: (C$_{19}$H$_{20}$N$_2$O$_3$): calc.: C: 70.35; H: 6.21; N: 8.64; exp.: C: 70.22; H: 6.27; N: 8.56

HPLC purity: 99.9%

Note: a fraction of E/Z mixture (470 mg) was isolated as well.

Example III tert-butyl {[(2S,4EZ)-1-(1,1'-biphenyl-4-ylcarbonyl)-4-(methoxyimino) pyrrolidin-2-yl]methoxy}acetate (5) (Compound of Formula Ia)

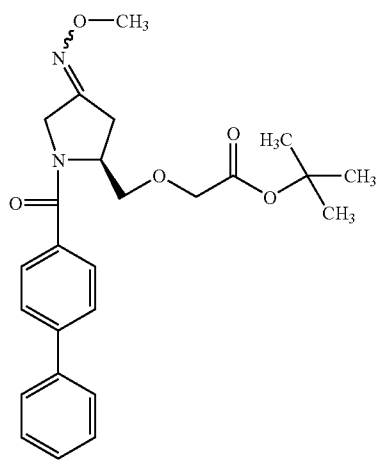

(5)

To a stirred solution of alcohol (2) (EZ mixture, 58 mg, 0.18 mmol) and tert-butyl bromoacetate (530 μl, 3.6 mmol) in dichloromethane (0.2 ml) were added 50% aqueous NaOH (0.8 ml) and tetrabutylammonium chloride (50 mg, 0.18 mmol) at room temperature, and the whole reaction mixture was stirred for 1 hour. After dilution with water, the mixture was extracted with ethyl acetate, organic phase was washed with brine, dried (MgSO$_4$) and concentrated. The product (compound 5) was purified by silica gel column chromatography using DCM:MeOH, 95:5 as eluant.

Yield: 99% (85 mg)

LC/MS (ESI, −): 381 (M-tBu-H)

$^1$H NMR (CDCl$_3$): 1.45 (s, 9H), 2.94 (m, 2H), 3.60–4.20 (m, 8H), 4.36 (m, 1H), 4.90 (m, 1H), 7.30–7.70 (m, 9H).

HPLC purity: 92%

Example IV

{[(2S,4EZ)-1-(1,1'-biphenyl-4ylcarbopyl)-4-(methoxyimino)pyrrolidin-2-yl]methoxy}acetic acid (6) (Compound of Formula Ia)

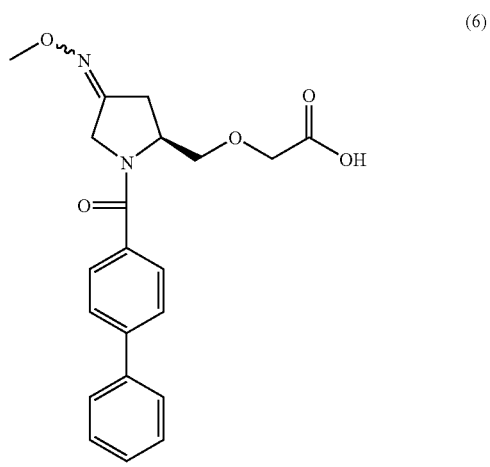

(6)

To a solution of tert-butyl ester (5) (45 mg, 0.1 mmol) in dichloromethane (0.5 ml) was added trifluoroacetic acid (0.1 ml) at room temperature. Once the reaction was completed, the mixture was concentrated in vacuo. The crude was dissolved in dichloromethane and washed with HCl 1M. The organic layer was dried (MgSO$_4$) and concentrated.

Yield: 40% (20 mg)

LC/MS (ESI−): 381 (M−H) (ESI+): 383 (M+H)

HPLC purity: 74%

Example V

2-{[(2S,4EZ)-1-(1,1'-biphenyl-4-ylcarbonyl)-4-(methoxyimino)pyrrolidin-2-yl]methoxy}-N-(2-pyrrolidin-1-ylethyl)acetamide (7) (Compound of Formula Ia)

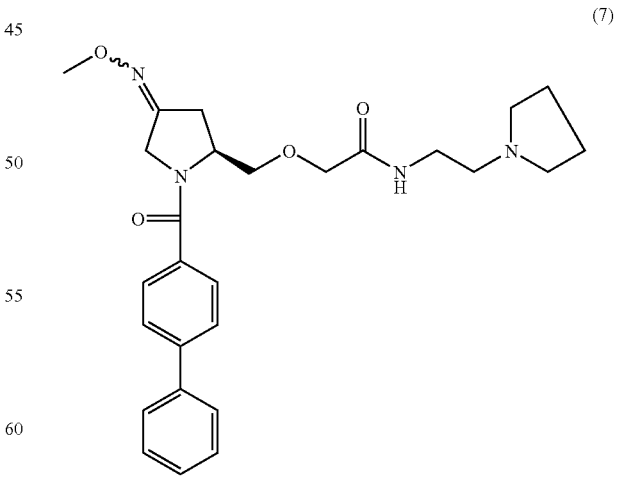

(7)

A solution of acid (6) (15 mg, 0.04 mmol), 1-(2-aminoethyl)-pyrrolidine (6 μl, 0.05 mmol), DIC (7.2 μl, 0.05 mmol) and DMAP (1 mg, 0.01 mmol) in dichloromethane (1 ml) was stirred under argon at room temperature for 18 hours. The mixture was concentrated in vacuo and purified on silica gel preparative chromatography using DCM:MeOH, 50:50 as eluant.

Yield: 80% (17 mg)

$^1$H NMR (CDCl$_3$): 1.71 (s, 4H), 2.30–4.00 (m, 8H), 3.37 (m, 2H), 3.50–4.40 (m, 9H), 4.96 (m, 1H), 6.87 (m, 1H), 7.30–7.70 (m, 9H)

LC/MS (ESI–): 477 (M–H) (ESI+): 479 (M+H)

HPLC purity: 88%

Example VI (3EZ,5S)-1-(1,1'-biphenyl-4-ylcarbonyl)-5-(methoxymethyl)pyrrolidin-3-one O-methyloxime (8) (Compound of Formula Ia) (8)

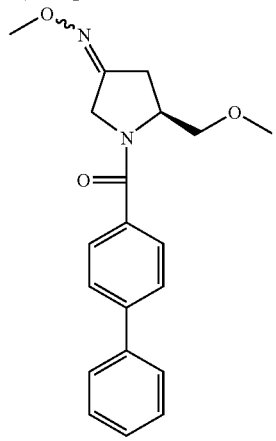

To a solution of alcohol (2) (EZ mixture, 20 mg, 0.06 mmol) and sodium hydride (3 mg, 0.12 mmol) in tetrahydrofuran (1 ml) under argon, was added methyl iodide (7.7 μl, 0.12 mmol). The reaction mixture was stirred overnight and quenched with water. The mixture was diluted with ethyl acetate and washed with brine, dried (MgSO$_4$) and concentrated in vacuo. The crude was purified on silica gel preparative chromatography using DCM: MeOH 100:0 then 95:5.

Yield: 94% (21 mg)

$^1$H NMR (CDCl$_3$): 2.80 (m, 2H), 3.35 (m, 3H), 3.46 (m, 1H), 3.67 (m, 1H), 3.84 (s, 3H), 4.27 (m, 2H), 4.91 (m, 1H), 7.30–7.70 (m, 9H).

LC/MS (ESI+): 339 (M+1)

HPLC purity: 93%

Example VII (3EZ,5S)-1-(1,1'-biphenyl-4-ylcarbonyl)-5-[(4-methylpiperazin-1-yl)methyl]pyrrolidin-3-one O-methyloxime (9) (Compound of Formula Ib) (9)

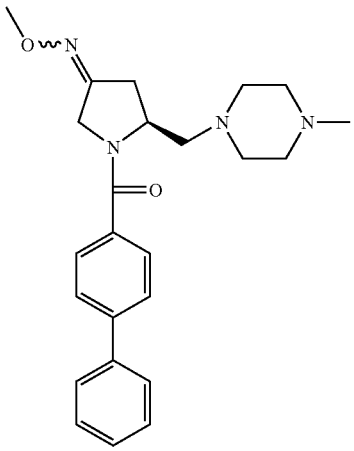

Intermediate 9a: [(2S, 4EZ)-1-(1,1'-biphenyl-4-ylcarbonyl)-4-(methoxyimino)pyrrolidin-2-yl]methyl methanesulfonate (Compound of Formula IIa). (9a)

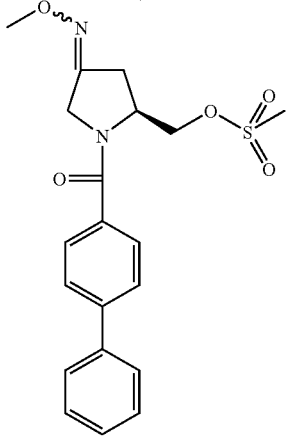

Mesyl chloride (48 μl, 0.62 mmol) was added to a solution of alcohol (2) (EZ mixture, 80 mg, 0.25 mmol) in DCM (8 ml) cooled at 0° C. and maintained under nitrogen atmosphere. The reaction mixture was then allowed to warm to r.t. and monitored by tlc. Completion was achieved after 1 h30. Organic phase was washed with saturated ammonium chlorid solution and brine, dried over magnesium sulfate, filtered and concentrated.

Yield: quant. (115 mg)

HPLC purity: 87%

Example VII: the mesylate (9a) (60 mg, 0.15 mmol) was dissolved in MEK/ACN (1:1, 10 ml) and treated with lithium bromid (16 mg, 0.18 mmol). The reaction mixture was heated at 85° C. before the addition of N-methylpiperazine (22 mg, 0.22 mmol) and TEA (31 μl, 0.22 mmol) and stirred at this temperature overnight. It was then concentrated, redissolved in Ethyl Acetate and washed with saturated NaHCO$_3$ solution, brine, dried over magnesium sulfate, filtered and concentrated. The crude (48 mg) was finally purified by flash chromatography with DCM/MeOH/NH$_4$OH 92:8:1 to give compound 9a.

Rf: 0.17 (DCM/MeOH/NH$_4$OH 90:10:1)

Yield: 36% (22 mg)

Appearance: brown oil

1H NMR (CDCl3): 2.31 (s, 3H), 2.45–2.86 (m, 14H), 3.85 (brs, 3H), 4.13 (m, 1H), 7.34–7.64 (m, 9H).

LC/MS (ESI, +): 407 (M+1)

HPLC purity: 97.1%

Example VIII (3EZ,5S)-1-(1,1'-biphenyl-4-ylcarbonyl)-5-{[(4-methoxyphenyl) amino]methyl}pyrrolidin-3-one O-methyloxime (10) (Compound of Formula Ib) (10)

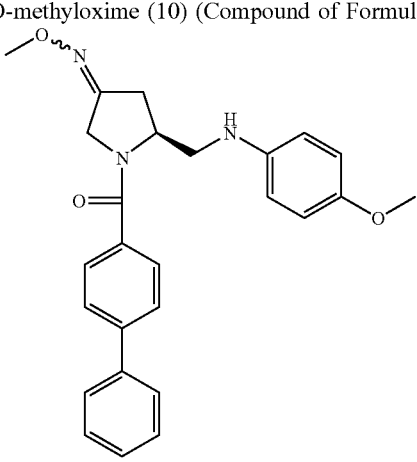

A solution of mesylate (9a) (32 mg, 0.08 mmol), p-methoxy aniline (20 mg, 0.16 mmol) and triethylamine (22 µl, 0.16 mmol) in methyl ethyl ketone/acetonitrile (2 ml, 1:1) was stirred for 2 days. The reaction mixture was diluted with ethyl acetate and washed wit $NH_4Cl$ sat. The organic phase was dried ($MgSO_4$) and concentrated. The crude thus obtained was purified by HPLC using a PARALLEX FLEX® system.

Yield: 21% (10 mg)
HPLC purity: 72%
LC/MS (ESI+): 430 (M+1)

Example IX (3EZ,5S)-1-(1,1'-biphenyl-4-ylcarbonyl)-5-({[2-(1H-pyrazol-1-yl) ethyl]amino}methyl)pyrrolidin-3-one O-methyloxime (11) (Compound of Formula Ib)

(11)

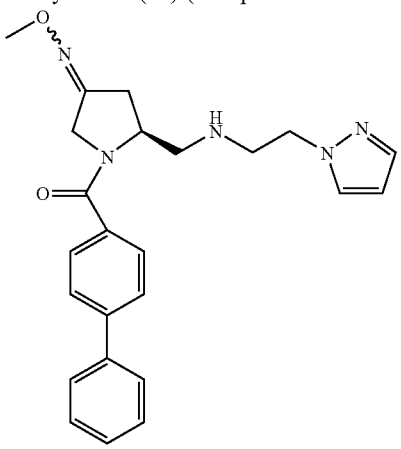

A solution of mesylate (9a) (60 mg, 0.15 mmol), 1-(2'-aminoethyl) pyrazole (58 mg, 0.53 mmol), potassium carbonate (41 mg, 0.30 mmol) and sodium iodide (225 mg, 1.50 mmol) in tetrahydrofuran (5 ml) was stirred for 2 days. The reaction mixture was diluted with ethyl acetate and washed with HCl 1N, then with brine. The organic phase was dried ($MgSO_4$) and concentrated. The crude was purified using a C8 SPE cartridge.

Yield: 5% (3 mg).
LC/MS (ESI+): 418 (M+H)
HPLC purity: 79%.

Example X

2-{[(2S,4EZ)-1-(1,1'-biphenyl-4-ylcarbonyl)-4-(methoxyimino)pyrrolidin-2-yl]methyl}-1H-isoindole-1,3(2H)-dione (12) (Compound of Formula Ib)

(12)

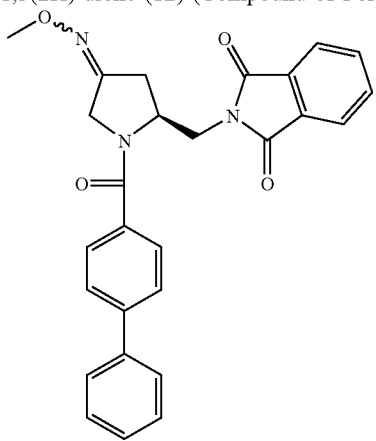

A solution of alcohol (2) (EZ mixture, 51 mg, 0.16 mmol), phtalimide (70 mg, 0.48 mmol), triphenylphosphine polymer bound (158 mg, 0.48 mmol) and diethyl azodicarboxylate (40% in toluene, 205 µl, 0.48 mmol) in tetrahydrofuran (5 ml) was stirred for 2 days. The resin was filtered off and the reaction mixture was concentrated in vacuo. The crude was purified on silica gel preparative chromatography using DCM as eluant.

Yield: 59% (50 mg).
$^1$H NMR ($CDCl_3$): 2.76 (m, 2H), 3.60–4.50 (m, 7H), 5.32 (m, 1H), 7.20–8.00 (m, 13H).
LC/MS (ESI+): 454 (M+1)
HPLC purity: 85%

Example XI (3EZ,5S)-5-(aminomethyl)-1-(1,1'-biphenyl-4-ylcarbonyl)pyrrolidin-3-one O-methyloxime (13) (Compound of Formula III)

(13)

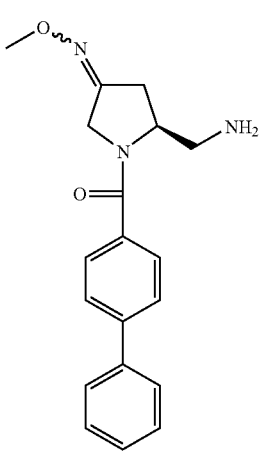

A solution of phtalimide (12) (42 mg, 0.09 mmol), hydrazine monohydrate (45 µl, 0.93 mmol) in ethanol: tetrahydrofuran (1:1, 1 ml) was stirred overnight. The white precipitate was filtered off and the filtrate was concentrated in vacuo to give the expected amine.

Yield: 76% (26 mg)
LC/MS (ESI−): 422 (M−1) (ESI+): 424 (M+1)
$^1$H NMR ($CDCl_3$): 2.29 (m, 1H), 2.70 (m, 1H), 3.43 (m, 1H), 3.64 (m, 3H), 3.83 (s, 3H), 4.17 (m, 1H), 6.90 (m, NH2), 7.20–8.00 (m, 9H).
HPLC purity: 88%.

Example XII

N-{[(4EZ,2S)-1-(1,1'-biphenyl-4-ylcarbonyl)-4-(methoxyimino)pyrrolidin-2-yl]methyl}acetamide (14) (Compound of Formula Ib)

(14)

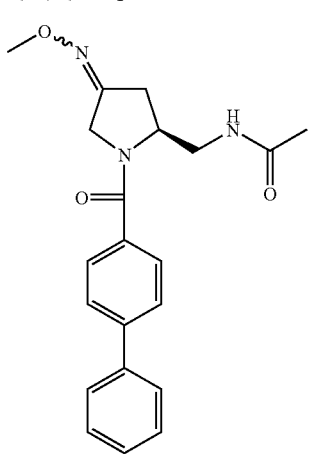

A solution of amine (13) (16 mg, 0.05 mmol), acetic anhydride (5.6 μl, 0.06 mmol) and triethylamine (7.9 μl, 0.06 mmol) in dichloromethane was stirred 30 min. The reaction mixture was washed with water. The organic phase was dried (MgSO$_4$) and concentrated in vacuo. The crude was purified on silica gel preparative chromatography using Ethyl acetate as eluant.

Yield: 42% (8 mg).

LC/MS (ESI−): 364 (M−1) (ESI+): 366 (M+1)

$^1$H NMR (CDCl$_3$): 2.10 (s, 3H), 2.40–3.00 (m, 2H), 3.54 (m, 2H), 3.87 (s, 3H), 4.24 (m, 2H), 4.81 (m, 1H), 7.20–8.00 (m, 9H).

HPLC purity: 95%.

Example XIII (3EZ,5S)-1-(1,1'-biphenyl-4-ylcarbonyl)-5-(piperidin-1-ylmethyl) pyrrolidin-3-one O-methyloxime (15) (Compound of Formula Ib)

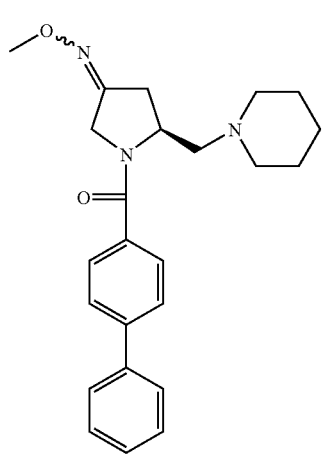

(15)

Intermediate 15a: methyl (4R)-1-(1,1'-biphenyl-4-ylcarbonyl)-4-{[tert-butyl (dimethyl) silyl]oxy}-L-prolinate (Compound of Formula VIII).

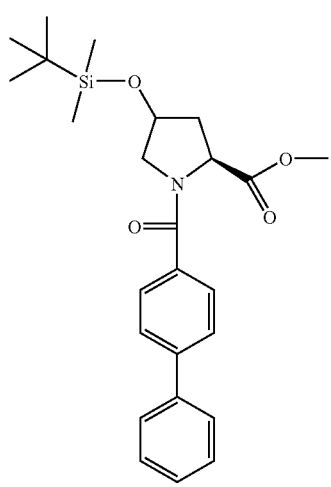

(15a)

Methyl (4R)-1-(1,1'-biphenyl-4-ylcarbonyl)-4-hydroxy-L-prolinate (intermediate 2a, 2.07 g, 6.35 mmol) was dissolved in DCM (30 ml) and treated with 4-DMAP (776 mg, 6.35 mmol), TEA (2.21 ml, 15.88 mmol) and TBDMS-Cl (1.91 g, 12.7 mmol). The reaction was monitored by LC/MS. After 24 h, as the reaction was not completed, TBDMS-CL (300 mg, 2 mmol) and TEA (1 ml) were added. After 48 h, the reaction was completed. The mixture was washed with sat. NH$_4$Cl and brine (twice), dried over magnesium sulfate, filtered and concentrated. The crude (2.85 g) was purified by flash chromatography using EtOAc/cHex 50:50 as eluant.

Yield: 93% (2.61 g)

1H NMR (CDCl3): −0.05 (s, 3H), 0.02 (s, 3H), 0.81 (s, 9H), 2.04 (m, 1H), 2.27 (m, 1H), 3.45 (d, J=9.4 Hz, 1H), 3.78 (s, 3H), 3.81 (m, 1H), 4.43 (m, 1H), 4.80 (t, J=8.1 Hz, 1H), 7.33–7.46 (m, 3H), 7.62 (m, 6H).

Intermediate 15b: ((2S,4R)-1-(1,1'-biphenyl-4-ylcarbonyl)-4-{[tert-butyl (dimethyl) silyl]oxy}pyrrolidin-2-yl)methanol.

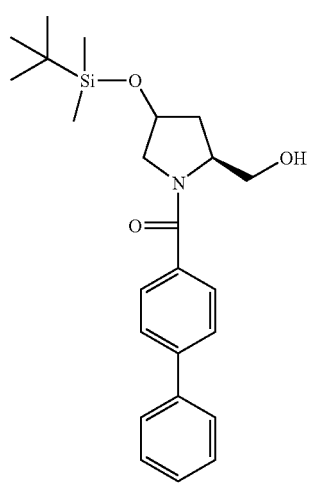

(15b)

A solution of methyl (4R)-1-(1,1'-biphenyl-4-ylcarbonyl)-4-{[tert-butyl (dimethyl) silyl]oxy}-L-prolinate (intermediate 15a, 2.61 g, 5.94 mmol) in THF (60 ml) was cooled to 0° C. and treated with lithium borohydride (95%, 206 mg, 8.9 mmol). The reaction mixture was stirred for 3 h and quenched slowly with water. THF was removed under reduced pressure, the crude was redissolved in AcOEt, washed with sat. NH$_4$Cl, brine, dried over magnesium sulfate, filtered and concentrated.

Yield: 92% (2.268 g)

LC/MS (ESI+): 412 (M+1)−

Intermediate 15c: 1-[((2S,4R)-1-(1,1'-biphenyl-4-ylcarbonyl)-4-{[tert-butyl (dimethyl) silyl]oxy}pyrrolidin-2-yl)methyl]piperidine (Compound of Formula XI)

(15c)

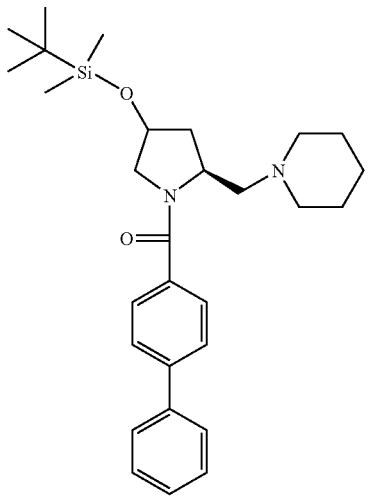

To a solution of alcohol (15b) (200 mg, 0.49 mmol) in dichloromethane (5 ml) under argon, was added Dess Martin reagent (227 mg, 053 mmol). The reaction mixture was stirred for 24 hours, then was diluted with dichloromethane and washed with NaHCO$_3$ sat. The aqueous layer was extracted with dichloromethane. The organic phases were washed with water, dried (MgSO$_4$) and concentrated. The aldehyde obtained was directly engaged in the following step. To a solution of aldehyde (184 mg, 0.45 mmol) in 1,2-dichloroethane were added piperidine (49 μl, 0.50 mmol), acetic acid (28 μl, 0.50 mmol) and then sodium triacetoxyborohydride (143 mg, 0.68 mmol). The reaction was stirred over night and then diluted with ethyl acetate. The organic phase was washed with sat. NaHCO$_3$, then with brine. The organic phase was dried (MgSO$_4$) and concentrated to afford the expected tertiary amine.

Yield: 95% (230 mg).

LC/MS (ESI−): 513 (M+Cl) (ESI+): 479 (M+1)

$^1$H NMR (CDCl$_3$): −0.09 (s, 3H), 0.00 (s, 3H), 0.79 (s, 9H), 1.20–1.60 (m, 6H), 2.08 (m, 4H), 2.40–2.90 (m, 4H), 3.35 (m, 1H), 3.56 (m, 1H), 4.34 (m, 1H), 4.59 (m, 1H), 7.20–7.60 (m, 9H).

HPLC purity: 90%.

Intermediate 15d: (3R,5S)-1-(1,1'-biphenyl-4-ylcarbonyl)-5-(piperidin-1-ylmethyl) pyrrolidin-3-ol (Compound of Formula XI)

(15d)

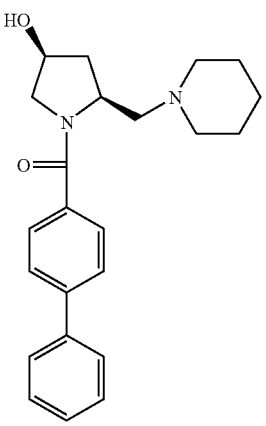

A solution of protected alcohol (15c) (200 mg, 0.42 mmol) and TBAF (0.63 ml, 1M in THF) in tetrahydrofuran was stirred at room temperature during 1 hour. The reaction mixture was concentrated and then diluted in acetone-ethyl acetate (1-2) and washed with a saturated NaHCO$_3$ solution. The organic phase was dried (MgSO$_4$) and concentrated to afford the expected alcohol.

Yield: 51% (90 mg).

LC/MS (ESI+): 365 (M+1)

$^1$H NMR (CDCl$_3$): 1.20–1.60 (m, 6H), 2.19 (m, 4H), 2.25–2.90 (m, 4H), 3.50 (m, 2H), 4.43 (m, 1H), 4.62 (m, 1H), 7.30–7.70 (m, 9H).

HPLC purity: 86%.

Intermediate 15e: (5S)-1-(1,1'-biphenyl-4-ylcarbonyl)-5-(piperidin-1-ylmethyl)-pyrrolidin-3-one (Compound of Formula X)

(15e)

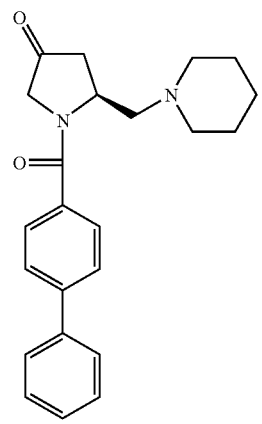

A solution of DMSO (46.8 μl, 0.66 mmol) in dichloromethane (1 ml) was added drop wise to a solution of oxalyl chloride (28.2 μl, 0.33 mmol) in dichloromethane (2 ml) at −78° C. under argon. After 15 min at −78° C., a solution of alcohol (15d) (80 mg, 0.22 mmol) in dichloromethane (1 ml) was added dropwise. The reaction mixture was stirred at −78° C. for 1 hour, treated with triethylamine (0.152 ml, 1.1 mmol) and allowed to warm to room temperature. The reaction mixture was diluted with ethyl acetate, washed with water then brine. The organic phase was dried (MgSO$_4$) and concentrated to afford the expected ketone.

Yield: 84% (78 mg).

LC/MS (ESI−): 361 (M−1) (ESI+): 363 (M+1)

HPLC purity: 86%.

Example XIII: A solution of ketone (15e) (70 mg, 0.19 mmol), hydroxylamine methyl ether hydrochloride (48 mg, 0.58 mmol) and triethylamine (80 μl, 0.58 mmol) in chloroforme (3 ml) was stirred at 70° C. for 2 days. The reaction mixture was diluted with dichloromethane and washed with HCl 1N. The organic phase was dried (MgSO$_4$) and concentrated to afford the oxime ether.

Yield: 90% (73 mg).

LC/MS (ESI+): 392 (M+1)

$^1$H NMR (CDCl$_3$): 1.39 (m, 2H), 1.50–1.90 (m, 4H), 2.07 (m, 2H), 2.43 (m, 2H), 2.50–3.10 (m, 4H), 3.38 (m, 1H), 3.68 (m, 1H), 3.79 (m, 3H), 4.21 (m, 2H), 4.86 (m, 1H), 7.20–8.00 (m, 9H).

HPLC purity: 94%.

Example XIV

(3EZ,5S)-1-(1,1'-biphenyl-4-ylcarbonyl)-5-(2-hydroxyethyl)pyrrolidin-3-one O-methyloxime (16) (Compound of Formula II)

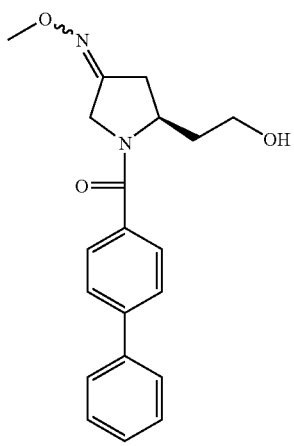

Intermediate 16a: [(2S,4R)-1-(1,1'-biphenyl-4-ylcarbonyl)-4-hydroxypyrrolidin-2-yl]acetic acid (Compound of Formula VIII)

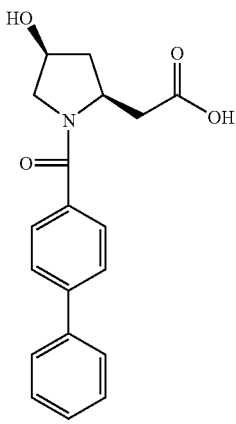

To a solution of commercial L-beta-homohydroxyproline hydrochloride (245 mg, 1.35 mmol), triethylamine (1.13 ml, 8.09 mmol) in water (0.8 ml) and tetrahydrofuran (2 ml) at 0° C. under argon, was added dropwise a solution of 4-phenylbenzoyl chloride (438 mg, 2.02 mmol) in tetrahydrofuran (1 ml). The reaction mixture was allowed to warm to room temperature and was stirred 18 hours. It was then diluted with acetone-ethyl acetate (1-2) and washed with HCl 1N. The organic phase was dried (MgSO$_4$) and concentrated to afford a mixture of desired product and 4-phenylbenzoyl acid. A small quantity of acid could be obtained by precipitation with ethyl acetate.

$^1$H NMR (DMSO): 1.82 (m, 1H), 2.11 (m, 1H), 2.5 (m, 1H), 2.81 (dd, J=15.6 Hz, J=3.2, 1H), 3.3 (m, 1H), 3.51 (dd, J=11.7 Hz, J=2.6 Hz, 1H), 4.16 (m, 1H), 4.40 (m, 1H), 7.30–8.00 (m, 9H).

LC/MS: (ESI−): 280 (M−1CO$_2$), 324 (M−1) (ESI+): 326 (M+1)

HPLC purity: 84%

Intermediate 16b: methyl [(2S,4R)-1-(1,1'-biphenyl-4-ylcarbonyl)-4-hydroxy-pyrrolidin-2-yl]acetate (Compound of Formula VIII)

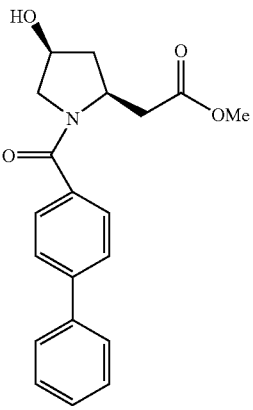

To a solution of the acid mixture previously obtained (intermediate 16a) in toluene-methanol (10 ml, 1-1) was added diazomethyltrimethylsilane (2.76 ml, 2M in hexane). After 3 hours, the reaction mixture was concentrated and purified by silica gel column chromatography using ethyl acetate as eluant.

Yield: 40% (for the two steps, 256 mg).

$^1$H NMR (DMSO): 1.82 (m, 1H), 2.11 (m, 1H), 2.6 (dd, J=15.4 Hz, J=8.3 Hz, 1H), 2.97 (dd, J=15.3 Hz, J=3.4 Hz, 1H), 3.25 (d, J=11.4 Hz, 1H), 3.62 (s, 3H), 3.67 (dd, J=11.4 Hz, J=3.4 Hz, 1H), 4.16 (m, 1H), 4.44 (m, 1H), 4.86 (d, J=3.4 Hz, OH) 7.30–8.00 (m, 9H).

LC/MS (ESI+): 340 (M+1)

HPLC purity: 98%.

Intermediate 16c: (3R,5R)-1-(1,1'-biphenyl-4-ylcarbonyl)-5-(2-hydroxyethyl)-pyrrolidin-3-ol (Compound of Formula VII)

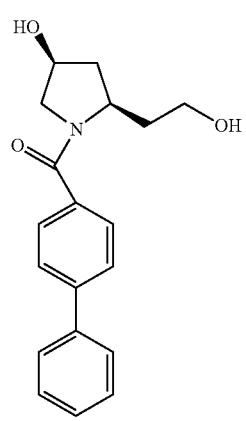

To a solution of methyl ester (16b) (310 mg, 0.91 mmol) in tetrahydrofuran at 0° C. umder argon, was added lithium borohydride (30 mg, 1.37 mmol). The reaction mixture was allowed to warm at room temperature and stirred 12 h. LiBH$_4$ was quenched with water and the tetrahydrofuran evaporated in vacuo. Acetonitrile was added and the white precipitate was filtered, washed with acetonitrile then with ether and finally dried.

Yield: 97% (280 mg)

¹H NMR (DMSO): 1.69 (m, 1H), 1.87 (m, 1H), 2.15 (m, 2H), 3.35 (m, 1H), 3.57 (m, 2H), 3.72 (d, J=11.3 Hz, 1H), 4.25 (m, 1H), 4.40 (m, 1H), 4.56 (m, OH), 4.87 (m, OH) 7.30–8.00 (m, 9H).

LC/MS (ESI+): 294 (M−H₂O+1), 312 (M+1)⁺, 334 (M+Na)

HPLC purity: 98.5%.

Intermediate 16d: (3R,5R)-1-(1,1'-biphenyl-4-ylcarbonyl)-5-(2-{[tert-butyl (dimethyl)silyl]oxy}ethyl)pyrrolidin-3-ol (Compound of Formula VII).

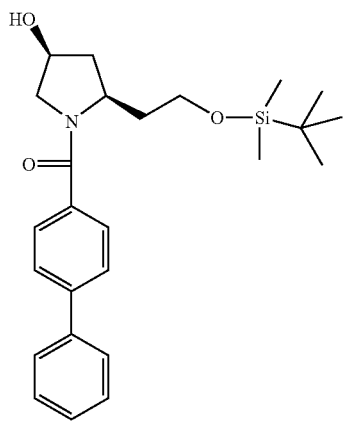

(16d)

To a solution of diol (16c) (270 mg, 0.87 mmol) in dimethylformamide (10 ml) was added dropwise a solution of tert-butyldimethylsilyl chloride (131 mg. 0.87 mmol) and triethylamine (120 μl, 0.87 mmol). The reaction mixture was stirred at room temperature for 2 days. Ethyl acetate was added and the reaction mixture was washed with water. The aqueous phase was extracted with ethyl acetate. The organic phases were dried (MgSO₄) and concentrated in vacuo. The crude was purified on silica gel preparative chromatography using Ethyl acetate: cyclohexane, 50:50 as eluant. Yield: 17% (63 mg).

LC/MS (ESI+): 426 (M+1)

HPLC purity: 100%.

Intermediate 16e: (5R)-1-(1,1'-biphenyl-4-ylcarbonyl)-5-(2-{[tert-butyl (dimethyl) silyl]oxy}ethyl)pyrrolidin-3-one (Compound of Formula IV).

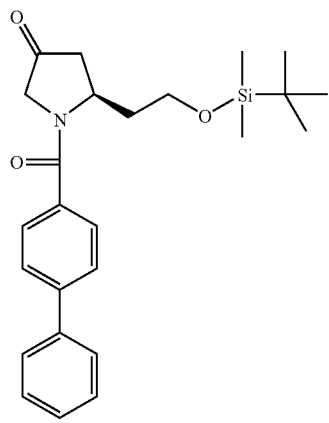

(16e)

A solution of DMSO (31.4 μl, 0.44 mmol) in dichloromethane (1 ml) was added drop wise to a solution of oxalyl chloride (19 μl, 0.22 mmol) in dichloromethane (2 ml) at −78° C. under argon. After 15 min at −78° C., A solution of alcohol (16d) (63 mg, 0.15 mmol) in dichloromethane (1 ml) was added dropwise. The reaction mixture was stirred at −78° C. for 1 hour and triethylamine (0.102 ml, 0.74 mmol) was added and allowed to warm to room temperature. The reaction mixture was diluted with ethyl acetate, washed with water then brine. The organic phase was dried (MgSO₄) and concentrated to afford the expected ketone.

Yield: 100% (64 mg).

LC/MS (ESI−): 422 (M−1) (ESI+): 424 (M+1)

HPLC purity: 99%.

Intermediate 16f: (3Z,5S)-1-(1,1'-biphenyl-4-ylcarbonyl)-5-(2-{[tert-butyl (dimethyl) silyl]oxy}ethyl)pyrrolidin-3-one O-methyloxime.

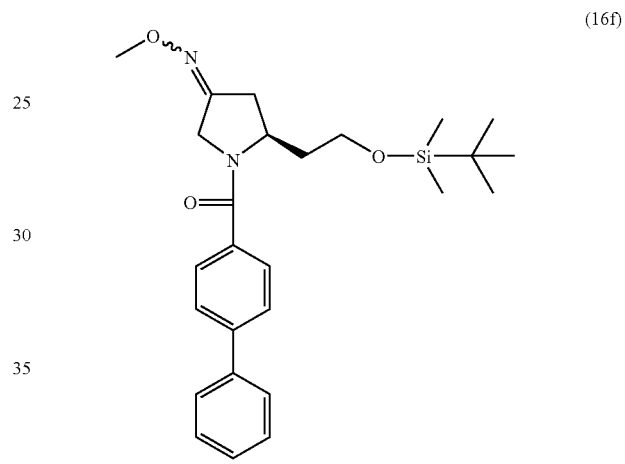

(16f)

A solution of ketone (16e) (64 mg, 0.15 mmol), hydroxylamine methyl ether hydrochloride (38 mg, 0.45 mmol) and triethylamine (62 μl, 0.45 mmol) in chloroform (4 ml) was stirred at 70° C. for 5 days. The reaction mixture was diluted with dichloromethane and washed with HCl 1N. The organic phase was dried (MgSO₄) and concentrated to afford the expected oxime ether.

Yield: 96% (68 mg).

¹H NMR (CDCl₃): 0.01 (s, 6H), 0.84 (s, 9H), 1.5–2.0 (m, 2H), 2.66 (m, 1H), 2.81 (m, 1H), 3.67 (m, 2H), 3.82 (s, 3 H), 4.20 (m, 2H), 4.88 (m, 1H), 7.20–8.00 (m, 9H).

HPLC purity: 95%.

LC/MS (ESI+): 453 (M+1)

Example XIV: A solution of protected alcohol (16f) (68 mg, 0.15 mmol) and TBAF (0.225 ml, 1M in THF) in tetrahydrofuran was stirred at room temperature during 1 hour. The reaction mixture was concentrated and then diluted in ethyl acetate and washed with water. The organic phase was dried (MgSO₄) and concentrated.

Yield: 85%.

¹H NMR (CDCl₃): 1.60 (m, 1H), 1.89 (m, 1H), 2.55 (m, 1H), 2.92 (m, 1H), 3.67 (m, 2H), 3.82 (s, 3 H), 4.20 (m, 2H), 5.07 (m, 1H), 7.20–8.00 (m, 9H).

LC/MS (ESI+): 339 (M+1)

HPLC purity: 96%.

Example XV

Preparation of a Pharmaceutical Formulation

The following Formulation examples illustrate representative pharmaceutical compositions according to the present invention being.

Formulation 1—Tablets

A pyrrolidine compound of Formula I is admixed as a dry powder with a dry gelatin binder in an approximate 1:2 weight ration. A minor amount of magnesium stearate is added as a lubricant. The mixture is formed into 240–270 mg tablets (80–90 mg of active pyrrolidine compound per tablet) in a tablet press.

Formulation 2—Capsules

A pyrrolidine compound of Formula I is admixed as a dry powder with a starch diluent in an approximate 1:1 weight ratio. The mixture is filled into 250 mg capsules (125 mg of active pyrrolidine compound per capsule).

Formulation 3—Liquid

A pyrrolidine compound of Formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A pyrrolidine compound of Formula I is admixed as a dry powder with a dry gelatin binder in an approximate 1:2 weight ratio. A minor amount of magnesium stearate is added as a lubricant. The mixture is formed into 450–900 mg tablets (150–300 mg of active pyrrolidine compound) in a tablet press.

Formulation 5—Injection

A pyrrolidine compound of Formula I is dissolved in a buffered sterile saline injectable aqueous medium to a concentration of approximately 5 mg/ml.

Example XVI

Biological Assays

The compounds according to Formula I may be subjected to the following assays:

a) In vitro Competition Binding Assay on hOT Receptor with Scintillation Proximity Assay (11).

This assay allows to determine the affinity of the test compounds for the human Oxytocin (hOT) receptor. Membranes from HEK293EBNA (cells expressing the hOT receptor) were suspended in buffer containing 50 mM Tris-HCl, pH 7.4, 5 mM MgCl2 and 0.1% BSA (w/v). The membranes (2–4 µg) were mixed with 0.1 mg SPA bead coated with wheat-germ aglutinin (WGA-PVT-Polyethylene Imine beads from Amersham) and 0.2 nM of the radiolabelled [$^{125}$I]-OVTA (OVTA being Ornithin Vasoactive, an analogue of OT for competitive binding experiments). Non-specific binding was determined in the presence of 1 µM Oxytocin. The total assay volume was 100 µl. The plates (Corning® NBS plate) were incubated at room temperature for 30 min and counted on a Mibrobeta® plate scintillation counter. Competitive binding was performed in presence of compounds of formula (I) at the following concentrations: 30 µM, 10 µM, 1 µM, 300 nM, 100 nM, 10 nM, 1 nM, 100 pM, 10 pM. The competitive binding data were analysed using the iterative, nonlinear, curve-fitting program, "Prism" (GraphPad Software, Inc).

The ability of pyrrolidine derivatives of formula (I) to inhibit the binding of $^{125}$-OVTA to the OT-receptor was assessed using the above described in vitro biological assay. Representative values for some example compounds are given in Table I where the binding affinity of test compounds from the above examples is expressed by the inhibition constant (Ki; nM). From these values, it can be derived that said test compounds according to formula I do show a significant binding to the oxytocin receptor.

TABLE I

| Compound No. | IUPAC-Name | Binding Affinity hOT-R (Ki [nM]) |
|---|---|---|
| 2 | (3EZ,5S)-1-(1,1'-biphenyl-4-ylcarbonyl)-5-(hydroxymethyl)pyrrolidin-3-one O-methyloxime | 139 |
| 4 | (3Z,5S)-1-(1,1'-biphenyl-4-ylcarbonyl)-5-(hydroxymethyl)pyrrolidin-3-one O-methyloxime | 94.9 |
| 7 | 2-{[(2S,4Z)-1-(1,1'-biphenyl-4-ylcarbonyl)-4-(methoxyimino)pyrrolidin-2-yl]methoxy}-N-(2-pyrrolidin-1-ylethyl)acetamide | 140 |
| 8 | (3EZ,5S)-1-(1,1'-biphenyl-4-ylcarbonyl)-5-(methoxymethyl)pyrrolidin-3-one O-methyloxime | 55.0 |
| 12 | 2-{[(2S,4Z)-1-(1,1'-biphenyl-4-ylcarbonyl)-4-(methoxyimino)pyrrolidin-2-yl]methyl}-1H-isoindole-1,3(2H)-dione | 5.1 |
| 16 | (3EZ,5S)-1-(1,1'-biphenyl-4-ylcarbonyl)-5-(2-hydroxyethyl)pyrrolidin-3-one O-methyloxime | 120 | b) Functional Assay No. 1: Inhibition of Oxytocin Mediated $Ca^{2+}$-mobilization by FLIPR® (Fluorimetric Imaging Plate Reader)

The action of OT-receptor triggers a complex cascade of events in the cell which leads to an increase in the intracytoplasmic $Ca^{2+}$ concentration. This increase in $Ca^{2+}$ concentration results from both calcium release from the sarcoplasmic reticulum (calcium stores) into the cytoplasm and from calcium influx from the extracellular space through $Ca^{2+}$ channels. This $Ca^{2+}$ mobilization into the cytoplasm triggers the contractile machinery of the myometrial cells which leads to uterine contractions (1 and 3).

This assay allows the measurement of the inhibition of OT/OT-R mediated calcium mobilization by test compounds of formula (I).

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates were pre-coated with PLL (Poly-L-Lysine) 10 µg/ml+0.1% gelatine to attach HEK293EBNA cells (Human Embryonic Kidney cells expressing the hOT receptor) and incubated for 30 min up to 2 days at 37° C. The cells were plated out into 96-well-plates (60000 cells/well).

Labelling with fluo-4: 50 µg of fluo-4 (Ca2+ sensitive fluorescent dye) were dissolved in 20 µl pluronic acid (20% in DMSO). The dissolved fluo-4 was then diluted in 10 ml DMEM (Dubecco's Minimal Essential Medium)-F12 culture medium. The plates were washed one time with DMEM-F12 medium. 100 µl of the fluo-4 containing-DMEM-F12 medium were added to the HEK-cells which were incubated for 1.5–2 h in this fluorescent medium. Fluo-4 is taken up by the cytoplasm of the cells.

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). The pH was adjusted to 7.4.

Performance of the assay: A minimum of 80 µl/well of compounds of formula (I) (5×) in the above buffer (1×) were prepared (96-well-plates). The compounds of formula (I) were added to the 96-well-plates at different concentrations (30 µM, 10 µM, 1 µM, 300 nM, 100 nM, 10 nM, 1 nM, 100 pM, 10 pM). OT was added at a concentration of 40 nM.

The relative fluorescence of Fluo-4 ($\lambda_{ex}$=488 nm, $\lambda_{em}$=590 nm) is then measured by the FLIPR in presence or absence of compounds of formula (I). The fluorescence of the marker being sensitive to the amount of $Ca^{2+}$, the $Ca^{2+}$ movements can be detected. Then, it can be determined the ability of compounds of formula (I) to antagonize the oxytocin-induced intracellular $Ca^{2+}$-mobilization mediated by the oxytocin receptor.

The activities of the pyrrolidine derivatives according to formula I were assessed using the above described in vitro biological assay. Representative values for some example compounds are given in Table II. The values refer to the concentration of the test compounds according to formula I necessary to antagonize by 50% the OT/OTR intracellular $Ca^{2+}$-mobilization. From the values, it can be derived that said example compounds according to formula I do exhibit a significant activity as oxytocin receptor antagonists.

TABLE II

| Compound No. | IUPAC-Name | Inhibition of Ca2+ mobilisation; hOT-RIC50 [µM] |
|---|---|---|
| 1 | (3EZ,5S)-5-(hydroxymethyl)-1-[(2'-methyl-1,1'-biphenyl-4-yl)carbonyl]pyrrolidin-3-one O-methyloxime | 0.03 |
| 2 | (3EZ,5S)-1-(1,1'-biphenyl-4-ylcarbonyl)-5-(hydroxymethyl)pyrrolidin-3-one O-methyloxime | 0.09 |
| 4 | (3Z,5S)-1-(1,1'-biphenyl-4-ylcarbonyl)-5(hydroxymethyl)pyrrolidin-3-one O-methyloxime | 0.01 | c) Functional Assay No. 2: Inhibition of IP3 (Inositol Tri-Phosphate)-Synthesis in HEK/EBNA-OTR Cells The interaction of OT on the OT-receptor leads to the IP3 synthesis, second messenger for $Ca^{2+}$ release from sarcoplasmic reticulum, involved in the uterine contraction triggering process (3).

This assay can be used to show the inhibition of the OT/OT-R mediated IP3 synthesis by using test compounds of formula (I).

Stimulation of the cells: HEK/EBNA OTR (rat or human) cells are plated out into costar 12-well plates, and equilibrated for 15–24 h with 4 µCi/ml radiolabelled [$^3$H]-Inositol with 1% FCS (0.5 ml/well) and without inositol supplement. The medium containing the label is aspirated. DMEM medium (without FCS, inositol), 20 mM Hepes (4-(2-hydroxyethyl)-1-piperazine-ethane-sulphonic acid), 1 mg/ml BSA containing 10 mM LiCl (freshly prepared), are added and incubated for 10–15 min at 37° C. The agonist (i.e. oxytocin used at a concentration of 10 nM) and the antagonists (i.e. the tests compounds of formula (I) can be used in a concentration of 10 µM, 1 µM, 300 nM, 100 nM, 10 nM, 1 nM, 100 pM, 10 pM, 3 pM) can be added at the required time (15–45 min), followed by aspiration of the medium. In the presence of OT, the radiolabelled inositol is converted to radiolabelled IP3. Antagonizing OT at the OT-receptor inhibits the IP3 formation.

The amount of the radiolabelled IP3 may be determined through the ensuing work-up. The reaction is stopped with 1 ml STOP-solution (i.e. 0.4 M perchloric acid), and let sit for 5–10 min at Room Temperature. Then, 0.8 ml are transferred into tubes containing 0.4 ml of neutralizing solution (0.72 M KOH/0.6M $KHCO_3$), and the tubes vortexed and kept in the cold at least for 2 h.

Separation of IP's: The samples are spun in a table top centrifuge at 3000–4000 rpm for 15 min. 1 ml of the supernatant is transferred to new tubes containing 2.5 ml $H_2O$. Packed resin (Dowex AG1X8) is equilibrated with 20 ml $H_2O$, and the whole samples are poured onto the chromatography columns, thus separating the mixture. To remove free inositol, two washes with 10 ml $H_2O$ are carried out.

Elution of total IP's: Elution is achieved using 3 ml 1M ammonium formate/0.1M formic acid. The eluant is collected in scintillation counting tubes, after the addition of 7 ml of scintillation liquid. The amount of [$^3$H]-IP3 is determined by a scintillating counter.

The ability of compounds of formula (I) to effectively antagonize oxytocin-induced IP3-synthesis mediated by the oxytocin receptor, can be assessed using the above described in vitro biological assay.

d) In vivo Model for Inhibition of Uterine Contractions

The assay evaluates the biological effect of tested compounds in an in vivo model of preterm labor, premature birth.

Non-pregnant Charles River CD (SD) BR female rats (9–10 weeks old, 200–250 g) were treated at 18 and 24 hours before the experiment with 250 µg/kg, i.p. diethylstilbestrol (DES). For the assay, the animal was anaesthetised with urethane (1.75 g/kg, i.p.) and placed on a homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P231ID Gould Statham pressure transducer.

One jugular vein was isolated, cannulated with a PE60 tubing and connected to a butterfly needle to provide an i.v. route of administration of the test compounds via a dispensing syringe.

In the case of intraduodenal administration of the test compounds, the duodenum can be isolated and similarly cannulated through a small incision in its wall.

One carotid artery was also isolated and cannulated with PE60 catheter and connected to a suitable syringe for blood sample collection.

After a stabilization period and throughout the experiment, the same dose of oxytocin was repeatedly injected intravenously at 30-min intervals. When reproducible contractile responses of the uterus to the same OT stimulus (selected dose of oxytocin) were obtained, the dose of the test or of the reference (vehicle) was administered. Further injection cycles of the same dose of oxytocin, were continued (OT injections at 30-min intervals) for a suitable time after treatment to assess the inhibitory effects and the reversibility of these effects.

The contractile response of the uterus to oxytocin was quantified by measuring the intra-uterine pressure and the number of contractions. The effect of the reference and test compounds was evaluated by comparing pre- and post-treatment pressure values. In addition, contractions of the uterine were measured at 5, 40, 75, 110, 145 and 180 minutes after test compound administration.

The activities of the pyrrolidine derivatives claimed in the Formula I can be assessed using the above described in vivo biological assay. Representative values for one example compound are given in Table III. The values refer to the capacity of the example compound according to Formula I to effectively antagonize oxytocin-induced uterine contractions in the rat when administered by either intravenous or oral route at 40 min after the test compound administration. From the values shown in Table III, it can be derived that said example test compound according to Formula I does exhibit a significant activity as tocolytic, i.e. uterine-relaxing, agent.

TABLE III

| Compound n°. | IUPAC-Name | % Reduction of Uterine Contraction | Doses [mg/kg] |
|---|---|---|---|
| 2 | (3Z,5S)-1-(1,1'-biphenyl-4-ylcarbonyl)-5-(hydroxymethyl)pyrrolidin-3-one O-methyloxime | 39.8 ± 10.0 | 10 (per i.v.) |
| 2 | (3Z,5S)-1-(1,1'-biphenyl-4-ylcarbonyl)-5-(hydroxymethyl)pyrrolidin-3-one O-methyloxime | 50.9 ± 8.6 | 30 (per os) |

REFERENCES

1. Gimpl G. and Fahrenholz, F. *Physiological Reviews* 2001, 81, 629–683
2. Maggi, M. et al. *J. Clin. Endocrinol. Metabol.* 1990, 70, 1142–1154.
3. Mitchell, B. F. and Schmid, B. *J. Soc. Gynecol. Invest.* 2001, 8,122–33.
4. Thorton, S. et al., *Experimental Physiology* 2001; 86, 297–302.
5. Evans B. E. et al. *J.Med.Chem.* 1992, 35, 3919–3927.
6. Gennaro, A. R. et al., Remington's Pharmaceutical Sciences. 18th ed. Easton: The Mack Publishing Company, 1995.
7. T. W. Greene et al. John Wiley & Sons Inc, Third Ed. 1999.
8. R. C. Larock, Wiley VCH 1999.
9. E. Breitmaier, W. Voelter Carbon-13 NMR Spectroscopy, 3rd Ed, p. 240, VCH, 1987.
10. Philip J. Kocienski, in *"Protecting Groups"*, Georg Thieme Verlag Stuttgart, New York, 1994.
11. Cook, N. D. et al. *Pharmaceutical Manufacturing International* 1992; p.49–53

The invention claimed is:

1. A pyrrolidine derivative of Formula I:

(I)

a geometrical isomer thereof, an optically active form thereof, an enantiomer thereof, a diastereomer thereof, one or more mixtures thereof, a racemate form thereof, or a salt thereof, wherein:

$R^1$ is selected from the group consisting of H and $C_1$–$C_6$-alkyl;

$R^2$ is selected from the group consisting of hydrogen, $C_1$–$C_6$-alkyl, $C_1$–$C_6$-alkyl aryl, heteroaryl, $C_1$–$C_6$-alkyl heteroaryl, $C_2$–$C_6$-alkenyl, $C_2$–$C_6$-alkenyl aryl, $C_2$–$C_6$-alkenyl heteroaryl, $C_2$–$C_6$-alkynyl, $C_2$–$C_6$-alkynyl aryl, $C_2$–$C_6$-alkynyl heteroaryl, $C_3$–$C_8$-cycloalkyl, heterocycloalkyl, $C_1$–$C_6$-alkyl cycloalkyl, $C_1$–$C_6$-alkyl heterocycloalkyl, $C_1$–$C_6$-alkyl carboxy, acyl, $C_1$–$C_6$-alkyl acyl, $C_1$–$C_6$-alkyl acyloxy, $C_1$–$C_6$-alkyl alkoxy, alkoxycarbonyl, $C_1$–$C_6$-alkyl alkoxycarbonyl, aminocarbonyl, $C_1$–$C_6$-alkyl aminocarbonyl, $C_1$–$C_6$-alkyl acylamino, $C_1$–$C_6$-alkyl ureido, amino, $C_1$–$C_6$-alkyl amino, sulfonyloxy, $C_1$–$C_6$-alkyl sulfonyloxy, sulfonyl, $C_1$–$C_6$-alkyl sulfonyl, sulfinyl, $C_1$–$C_6$-alkyl sulfinyl, $C_1$–$C_6$-alkyl sulfanyl, and $C_1$–$C_6$-alkyl sulfonylamino;

$R^3$ is selected from the group consisting of aryl and heteroaryl;

X is selected from the group consisting of O and $NR^4$;

$R^4$ is selected from the group consisting of H, $C_1$–$C_6$-alkyl, $C_1$–$C_6$-alkyl aryl, $C_1$–$C_6$-alkyl heteroaryl, aryl and heteroaryl; wherein $R^2$ and $R^4$ can form together with the N atom to which they are linked to, a 5–8 membered saturated or unsaturated heterocycloalkyl ring; and n is an integer from 1 to 3.

2. A pyrrolidine derivative according to claim 1, wherein $R^1$ is methyl.

3. A pyrrolidine derivative according to claim 1, wherein $R^3$ is a phenyl.

4. A pyrrolidine derivative according to claim 1, wherein n is an integer 1 or 2.

5. A pyrrolidine derivative according to claim 1 wherein $R^2$ and $R^4$ form together with the N atom to which they are linked, a 5 or 6 membered cycloalkyl or heterocycloalkyl ring.

6. A pyrrolidine derivative according to claim 1 wherein X is O or NH.

7. A pyrrolidine derivative according to claim 1, selected from the group consisting of:

(3EZ,5S)-5-(hydroxymethyl)-1-[(2'-methyl-1,1'-biphenyl-4-yl)carbonyl]pyrrolidin-3-one O-methyloxime;

(3EZ,5S)-1-(1,1'-biphenyl-4-ylcarbonyl)-5-(hydroxymethyl)pyrrolidin-3-one O-methyloxime;

(3E,5S)-1-(1,1'-biphenyl-4-ylcarbonyl)-5-(hydroxymethyl)pyrrolidin-3-one O-methyloxime;

(3Z,5S)-1-(1,1'-biphenyl-4-ylcarbonyl)-5-[(4-methylpiperazin-1-yl)methyl]pyrro-lidin-3-one O-methyloxime;

tert-butyl {[(2S,4EZ)-1-(1,1'-biphenyl-4-ylcarbonyl)-4-(methoxyimino)pyrrolidin-2-yl]methoxy}acetate;

{[(2S,4EZ)-1-(1,1'-biphenyl-4-ylcarbonyl)-4-(methoxyimino)pyrrolidin-2-yl]methoxy}acetic acid;

2-{[(2S,4EZ)-1-(1,1'-biphenyl-4-ylcarbonyl)-4-(methoxyimino)pyrrolidin-2-yl]methoxy}-N-(2-pyrrolidin-1-ylethyl)acetamide;

(3EZ,5S)-1-(1,1'-biphenyl-4-ylcarbonyl)-5-(methoxymethyl)pyrrolidin-3-one O-methyloxime;

(3EZ, 5S)-1-(1,1'-biphenyl-4-ylcarbonyl)-5-[(4-methylpiperazin-1-yl)methyl]pyrrolidin-3-one O-methyloxime;

(3EZ,5S)-1-(1,1'-biphenyl-4-ylcarbonyl)-5-{[(4-methoxyphenyl)amino]methyl}-pyrrolidin-3-one O-methyloxime;

(3EZ,5S)-1-(1,1'-biphenyl-4-ylcarbonyl)-5-({[2-(1H-pyrazol-1-yl)ethyl]amino}methyl)-pyrrolidin-3-one O-methyloxime;

2-{[(2S,4EZ)-1-(1,1'-biphenyl-4-ylcarbonyl)-4-(methoxyimino)pyrrolidin-2-yl]methyl}-1H-isoindole-1,3(2H)-dione;

(3EZ,5S)-5-(aminomethyl)-1-(1,1'-biphenyl-4-ylcarbonyl)pyrrolidin-3-one O-methyloxime;

N-{[(2S,4EZ)-1-(1,1'-biphenyl-4-ylcarbonyl)-4-(methoxyimino)pyrrolidin-2-yl]methyl}acetamide;

(3EZ,5S)-1-(1,1'-biphenyl-4-ylcarbonyl)-5-(piperidin-1-ylmethyl)pyrrolidin-3-one O-methyloxime; and (3EZ,5S)-1-(1,1'-biphenyl-4-ylcarbonyl)-5-(2-hydroxyethyl)pyrrolidin-3-one O-methyloxime.

8. A method of treating preterm labor, premature birth or dysmenorrhea, said method comprising administering said pyrrolidine derivative according to claim 1 to a patient in need thereof in an amount sufficient to treat said preterm labor, said premature birth or said dysmenorrhea.

9. A pharmaceutical composition comprising said pyrrolidine derivative according to claim 1 and a pharmaceutically acceptable carrier, diluent or excipient thereof.

10. A process for the preparation of said pyrrolidine derivative according to claim 1 wherein X is O, comprising O-alkylating an alcohol derivative of formula (II) with an alkylating agent $R^2$-LG wherein LG is a leaving group

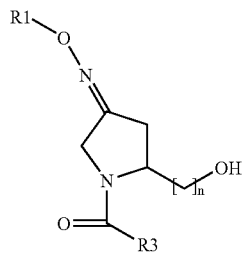

II to obtain said pyrrolidine derivative.

11. A process for the preparation of said pyrrolidine derivative according to claim 1 wherein X is $NR^4$, comprising reductively aminating an aldehyde derivative of formula (XI) with an amine $HNR^2R^4$

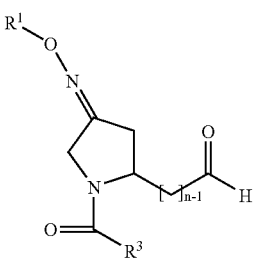

XI to obtain said pyrrolidine derivative.

* * * * *

UNITED STATES PATENT AND TRADEMARK OFFICE
CERTIFICATE OF CORRECTION

PATENT NO.        : 7,115,754 B2                                Page 1 of 4
APPLICATION NO.   : 10/518543
DATED             : October 3, 2006
INVENTOR(S)       : Catherine Jorand-Lebrun et al.

It is certified that error appears in the above-identified patent and that said Letters Patent is hereby corrected as shown below:

Column 5, line 21, " (e.g., norborn yl). " should read -- (e.g., norbornyl). --.

Column 6, line 55, " "($C_1$-$C_6$-alkyl aryl" " should read -- "$C_1$-$C_6$-alkyl aryl" --.

Column 9, line 27, " methyloxy-phenyl goup, " should read -- methyloxy-phenyl group, --.

Column 17, formula XVI, "                                          "

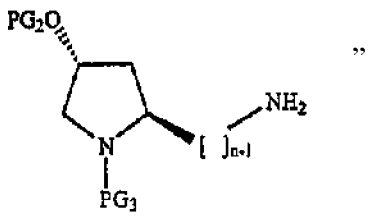

should read --  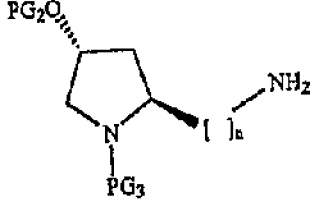  --;

UNITED STATES PATENT AND TRADEMARK OFFICE
CERTIFICATE OF CORRECTION

PATENT NO. : 7,115,754 B2
APPLICATION NO. : 10/518543
DATED : October 3, 2006
INVENTOR(S) : Catherine Jorand-Lebrun et al.

It is certified that error appears in the above-identified patent and that said Letters Patent is hereby corrected as shown below:

Column 17, formula XVIII, " 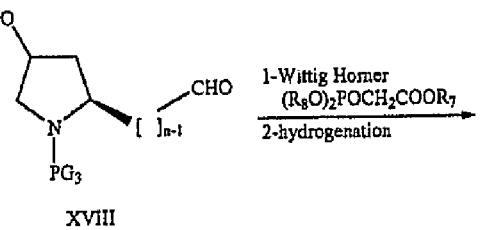 "

should read -- 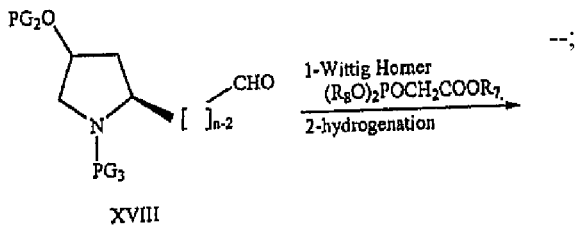 --;

Column 18, formula XIX, " 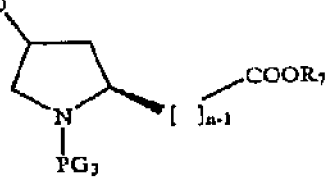 "

should read -- 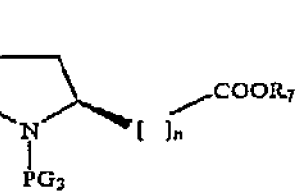 --;

line 30, "as outlined is Scheme 10." should read -- as outlined in Scheme 10. --.

UNITED STATES PATENT AND TRADEMARK OFFICE
CERTIFICATE OF CORRECTION

PATENT NO. : 7,115,754 B2
APPLICATION NO. : 10/518543
DATED : October 3, 2006
INVENTOR(S) : Catherine Jorand-Lebrun et al.

It is certified that error appears in the above-identified patent and that said Letters Patent is hereby corrected as shown below:

Column 19, Scheme 11, line 19 " 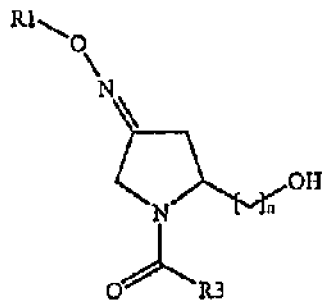 "

should read -- 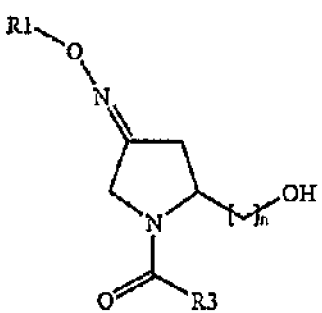 --;

Column 23, line 15, " (Z)isomers could " should read -- (Z)-isomers could --.

Column 27, line 25, " Coupling the $R^3$ Moitey: " should read -- Coupling the $R^3$ Moiety: --.

Column 28, line 33, " (3EZ,5S-1-(1,1'-biphenyl-4-ylcarbonyl)-5 " should read -- (3EZ,5S)-l-(1,1'-biphenyl-4-ylcarbonyl)-5 --.

Column 30, line 64, " 2.49–2.7Θ " should read -- 2.49–2.70 --.

Column 35, line 8, " (EST+): 479 " should read -- (ESI+): 479 --.

UNITED STATES PATENT AND TRADEMARK OFFICE
CERTIFICATE OF CORRECTION

PATENT NO.        : 7,115,754 B2
APPLICATION NO. : 10/518543
DATED             : October 3, 2006
INVENTOR(S)       : Catherine Jorand-Lebrun et al.

It is certified that error appears in the above-identified patent and that said Letters Patent is hereby corrected as shown below:

Column 40, line 67, " 412 (M+1)- " should read -- 412 (M+1) --.

Column 41, line 26, " (227 mg, 053 mmol). " should read -- (227 mg, 0.53 mmol). --.

Column 43, line 66, " 280 (M-1 $CO_2$), " should read -- 280 (M-1-$CO_2$), --.

Column 48, line 5, " binding of $^{125}$-OVTA " should read -- binding of $^{125}$I-OVTA --.

Column 52, line 62, " (3EZ,    5S)-1-(1,1'-biphenyl-4-ylcarbonyl)-5-[(4-meth- "
           Should read -- (3EZ,5S)-1-(1,1'-biphenyl-4-ylcarbonyl)-5-[(4-meth- --.

Signed and Sealed this

Eighteenth Day of September, 2007

JON W. DUDAS
*Director of the United States Patent and Trademark Office*